(12) United States Patent
Brodney et al.

(10) Patent No.: US 7,163,942 B2
(45) Date of Patent: Jan. 16, 2007

(54) SULFONAMIDE COMPOUNDS FOR THE TREATMENT OF NEURODEGENERATIVE DISORDERS

(75) Inventors: Michael A. Brodney, East Lyme, CT (US); Karen J. Coffman, Pawcatuck, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 11/078,739

(22) Filed: Mar. 11, 2005

(65) Prior Publication Data

US 2005/0222254 A1    Oct. 6, 2005

Related U.S. Application Data

(60) Provisional application No. 60/558,660, filed on Apr. 1, 2004.

(51) Int. Cl.
| | | |
|---|---|---|
| A61K 31/18 | (2006.01) | |
| C07C 311/20 | (2006.01) | |
| C07C 311/21 | (2006.01) | |

(52) U.S. Cl. .................. 514/238.2; 514/311; 514/361; 514/364; 514/374; 514/381; 514/522; 514/539; 514/603; 514/604; 544/160; 548/127; 548/131; 548/235; 548/253; 558/42; 558/43; 560/13; 564/85; 564/86; 564/87; 564/88; 564/89; 564/90; 564/92

(58) Field of Classification Search ............. 514/235.2, 514/311, 361, 364, 374, 381, 522, 539, 603, 514/604; 544/160; 548/127, 131, 235, 253, 548/42, 43; 560/13; 564/85, 86, 87, 88, 564/89, 90, 92
See application file for complete search history.

(56) References Cited

U.S. PATENT DOCUMENTS 5,491,170 A * 2/1996 Lee et al. .................... 514/538

FOREIGN PATENT DOCUMENTS

| EP | 0606046 | | 12/1993 |
|---|---|---|---|
| EP | 0967201 | | 12/1999 |
| JP | 48004784 | * | 2/1973 |
| WO | 9620689 | | 7/1996 |
| WO | WO 03051825 | | 6/2003 |
| WO | WO 03053912 | | 7/2003 |

OTHER PUBLICATIONS

Wiley et al, J. Chem. Soc., 1952, 74, 936-938.*

* cited by examiner

*Primary Examiner*—Shailendra Kumar
(74) *Attorney, Agent, or Firm*—Steve Zelson; James A. Jubinsky

(57) ABSTRACT

The present invention relates to compounds of the Formula I

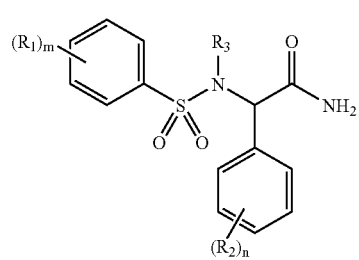

wherein $R^1$, $R^2$, $R^3$, m, and n are as defined. Compounds of the Formula I have activity inhibiting production of Aβ-peptide. The invention also relates to pharmaceutical compositions and methods for treating disorders and diseases, for example, neurodegenerative and/or neurological disorders, e.g., Alzheimer's disease, in a mammal comprising compounds of the Formula I.

18 Claims, No Drawings

SULFONAMIDE COMPOUNDS FOR THE TREATMENT OF NEURODEGENERATIVE DISORDERS

CROSS REFERENCE TO RELATED APPLICATION

The present application claims benefit of U.S. Ser. No. 60/558,660 filed on Apr. 1, 2004, which is incorporated by reference herein in its entirety.

FIELD OF THE INVENTION

The present invention relates to the treatment of neurodegenerative and/or neurological disorders, such as Alzheimer's disease, in mammals, including humans. This invention also relates to inhibiting, in mammals, including humans, the production of Aβ-peptides that can contribute to the formation of neurological deposits of amyloid protein. More particularly, this invention relates to sulfonamide compounds, pharmaceutical compositions comprising such compounds and methods of using such compounds, i.e., for the treatment of neurodegenerative and/or neurological disorders, such as Alzheimer's disease, related to Aβ-peptide production.

BACKGROUND OF THE INVENTION

Dementia results from a wide variety of distinctive pathological processes. The most common pathological processes causing dementia are Alzheimer's disease (AD), cerebral amyloid angiopathy (CAA) and prion-mediated diseases. AD affects nearly half of all people past the age of 85, the most rapidly growing portion of the United States population. As such, the number of AD patients in the United States is expected to increase from about 4 million to about 14 million by the middle of the next century.

Treatment of AD typically is the support provided by a family member in attendance. Stimulated memory exercises on a regular basis have been shown to slow, but not stop, memory loss. A few drugs, for example Aricept™, provide treatment of AD.

A hallmark of AD is the accumulation in the brain of extracellular insoluble deposits called amyloid plaques and abnormal lesions within neuronal cells called neurofibrillary tangles. Increased plaque formation is associated with an increased risk of AD. Indeed, the presence of amyloid plaques, together with neurofibrillary tangles, is the basis for definitive pathological diagnosis of AD.

The major components of amyloid plaques are the amyloid Aβ-peptides, also called Aβ-peptides, that consist of several proteins including those having 38, 40, 42 or 43 amino acids, designated as the $A\beta_{1-38}$, $A\beta_{1-40}$, $A\beta_{1-42}$ and $A\beta_{1-43}$ peptides, respectively. The Aβ-peptides are thought to cause nerve cell destruction, in part, because they are toxic to neurons in vitro and in vivo.

The Aβ peptides are derived from larger amyloid precursor proteins (APP proteins), that consist of four proteins containing 695, 714, 751 or 771 amino acids, designated as the $APP_{695}$, $APP_{714}$, $APP_{751}$, and $APP_{771}$, respectively. Proteases are believed to produce the Aβ peptides by cleaving specific amino acid sequences within the various APP proteins. The proteases are named "secretases" because the Aβ-peptides they produce are secreted by cells into the extracellular environment. These secretases are each named according to the cleavage(s) they make to produce the Aβ-peptides. The secretase that forms the amino terminal end of the Aβ-peptides is called the beta-secretase. The secretase that forms the carboxyl terminal end of the Aβ-peptides is called the gamma-secretase.

This invention relates to novel compounds that inhibit Aβ-peptide production, to pharmaceutical compositions comprising such compounds, and to methods of using such compounds to treat neurodegenerative and/or neurological disorders.

SUMMARY OF THE INVENTION

The present invention relates to compounds of the Formula I

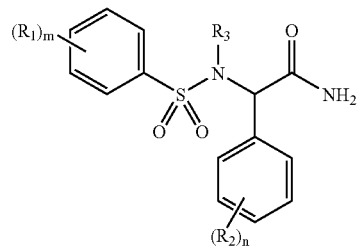

wherein $R^1$ and $R^2$ are each independently selected from —H, —$C_1$–$C_8$ alkyl, —$C_2$–$C_8$ alkenyl, —$C_1$–$C_8$ alkoxy, —$C_2$–$C_8$ alkenoxy, —$C_1$–$C_8$ hydroxyalkyl, —$C_2$–$C_8$ hydroxyalkenyl, -halo, —CN, —$NO_2$, —$(CH_2)qNC(=O)R^6$, —$(CH_2)qC(=O)OR^5$, —$(CH_2)qC(=O)NR^6R^7$, —$(CH_2)qNR^6R^7$, —$C_3$–$C_8$ cycloalkyl and —$C_5$–$C_8$ cycloalkenyl, wherein $R^1$ and $R^2$ are each optionally independently substituted with from one to three substituents independently selected from —$C_1$–$C_6$ alkoxy, —$C_1$–$C_6$ alkyl -halo and —OH;

$R^3$ is a group of the Formula II or the Formula III, each as depicted below

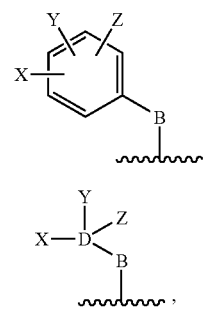

wherein B is absent or is selected from —$C_1$–$C_8$ alkylene and —$C_2$–$C_4$ alkenylene;

D is selected from —$C_1$–$C_8$ alkyl, —$C_3$–$C_{10}$ cycloalkyl, -(3–10 membered) heterocycloalkyl and -(5–7 membered) heteroaryl;

X, Y and Z are each independently selected from —H, —$C_1$–$C_8$ alkyl, —$C_2$–$C_8$ alkenyl, —$C_1$–$C_8$ alkoxy, —$C_2$–$C_8$ alkenoxy, —$C_1$–$C_8$ hydroxyalkyl, —$C_2$–$C_8$ hydroxyalkenyl, -halo, —OH, —CN, —$NO_2$, —$(CH_2)_q$—$NR^7R^8$, —$(CH_2)_q$—NHC(=O)$R^9$, —$(CH_2)_q$—C(=O)$R^9$, —$(CH_2)_Q$—C(=O)$NR^7R^8$, —$(CH_2)_q$—C(=O)$OR^9$, —$(CH_2)_q$—$SO_2R^9$, —S($C_1$–$C_8$ alkyl), —$C_3$–$C_8$ cycloalkyl, —(CH$_2$)$_q$—((3–10 membered) heterocycloalkyl), —(CH$_2$)$_q$—(C$_6$–C$_{14}$ aryl), —(CH$_2$)$_q$—((4–10 membered) heteroaryl) and —(CH$_2$)$_q$—(C$_6$–C$_{14}$ aryloxy);

wherein said X, Y and Z are each optionally independently substituted with from one to three substituents independently selected from —C$_1$–C$_8$ alkyl, —C$_2$–C$_8$ alkenyl, —C$_1$–C$_8$ alkoxy, —C$_2$–C$_8$ alkenoxy, C$_1$–C$_8$ hydroxyalkyl, —C$_2$–C$_8$ hydroxyalkenyl, halo, —OH and —CN;

and wherein said alkoxy substituent of X, Y and Z is optionally independently substituted with from one to three substituents independently selected from halo, preferably —F;

R$^5$, R$^6$ R$^7$, R$^8$ and R$^9$ are each independently selected from —H, —C$_1$–C$_{12}$ alkyl, —C$_2$–C$_{12}$ alkenyl, —C$_3$–C$_{10}$ cycloalkyl, —C$_5$–C$_{10}$ cycloalkenyl, —C$_5$–C$_{13}$ bicycloalkyl, —C$_7$–C$_{13}$ bicycloalkenyl, —(3–10 membered) heterocycloalkyl, —C$_6$–C$_{14}$ aryl and —(5–8 membered) heteroaryl;

wherein NR$^6$R$^7$ or NR$^7$R$^8$ may in each instance independently optionally form a —(3–8 membered) heterocycloalkyl;

m is 0, 1, 2 or 3;

n is 0, 1, 2 or 3;

q is 0, 1 or 2;

or the pharmaceutically acceptable salts of such compounds.

Compounds of the Formula I may have optical centers and therefore may occur in different enantiomeric and diastereomeric configurations. The present invention includes all enantiomers, diastereomers, and other stereoisomers of such compounds of the Formula I, as well as racemic compounds and racemic mixtures and other mixtures of stereoisomers thereof.

Pharmaceutically acceptable salts of the compounds of Formula I include the acid addition and base salts thereof.

Suitable acid addition salts are formed from acids which form non-toxic salts. Examples include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandelates mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, salicylate, saccharate, stearate, succinate, sulfonate, stannate, tartrate, tosylate, trifluoroacetate and xinofoate salts.

Suitable base salts are formed from bases which form non-toxic salts. Examples include, but are not limited to, the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include, but are not limited to, clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889–1896, by O. Almarsson and M. J. Zaworotko (2004). For a general review of multi-component complexes, see J Pharm Sci, 64 (8),1269–1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see Crystals and the Polarizing Microscope by N. H. Hartshorne and A. Stuart, 4$^{th}$ Edition (Edward Arnold, 1970).

Hereinafter all references to compounds of Formula I include references to salts, solvates, multi-component complexes and liquid crystals thereof and to solvates, multi-component complexes and liquid crystals of salts thereof.

The compounds of the invention include compounds of Formula I as hereinbefore defined, including all polymorphs and crystal habits thereof, prodrugs and isomers thereof (including optical, geometric and tautomeric isomers) as hereinafter defined and isotopically-labeled compounds of Formula I.

Unless otherwise indicated, as used herein, the term "B is absent" means a direct bond between the nitrogen and the other groups (e.g., —N—D).

Unless otherwise indicated, as used herein, the terms "halo" and "halogen" include F, Cl, Br and I.

Unless otherwise indicated, as used herein, the term "alkyl" includes saturated monovalent hydrocarbon radicals having straight or branched moieties. Examples of alkyl groups include, but are not limited to, methyl, ethyl, n-propyl, isopropyl and t-butyl.

Unless otherwise indicated, as used herein, the term "alkenyl" includes alkyl moieties having at least one carbon-carbon double bond wherein alkyl is as defined above. Examples of alkenyl include, but are not limited to, ethenyl and propenyl.

Unless otherwise indicated, as used herein, the term "alkylene" includes saturated, divalent hydrocarbon radicals i.e., generally present as a bridging group between two other groups, having straight or branched moieties. Examples of alkylene groups include —CH$_2$—(methylene); —CH$_2$CH$_2$—(ethylene); —CH$_2$CH$_2$CH$_2$—(propylene), —CH(CH$_3$)CH$_2$—(isopropylene) etc.

Unless otherwise indicated, as used herein, the term "alkenylene" includes divalent hydrocarbon radicals with at least one carbon-carbon double bond and may include straight or branched alkenylene groups, such as ethyenylene. Alkenylene groups are generally present as a bridging group between two other groups.

Unless otherwise indicated, as used herein, the term "cycloalkyl" includes non-aromatic saturated cyclic alkyl moieties wherein alky is as defined above. Examples of cycloalkyl include, but are not limited to, cyclopropyl, cyclobutyl, cyclopentyl, cyclohexyl and cycloheptyl. "Bicycloalkyl" and "tricycloalkyl" groups are non-aromatic saturated carbocyclic groups consisting of two or three rings respectively, wherein said rings share at least one carbon atom. Unless otherwise indicated, for purposes of the present invention, bicycloalkyl groups include spiro groups and fused ring groups. Examples of bicycloalkyl groups include, but are not limited to, bicyclo-[3,1,0]-hexyl, bicyclo-2,2,1]-hept-1-yl, norbornyl, spiro[4,5]decyl, spiro[4,4] nonyl, spiro[4,3]octyl, and spiro[4,2]heptyl. An example of a tricycloalkyl group is adamantanyl. Other cycloalkyl, bicycloalkyl and tricycloalkyl groups are known in the art, and such groups are encompassed by the definitions "cycloalkyl," "bicycloalkyl" and "tricycloalkyl" herein. "Cycloalkenyl," "bicycloalkenyl" and "tricycloalkenyl" refer to non-aromatic carbocyclic cycloalkyl, bicycloalkyl and tricycloalkyl moieties as defined above, except that cycloalkenyl, bicycloalkenyl and tricycloalkenyl comprise one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl, cyclobutenyl and cyclohexenyl, and a non-limiting example of a bicycloalkenyl group is norbornenyl. Cycloalkyl, cycloalkenyl, bicycloalkyl and bicycloalkenyl groups also include groups that are substituted with one or more oxo moieties. Examples of such groups with oxo moieties are oxocyclopentyl, oxocyclobutyl, oxocyclopentenyl and norcamphoryl. Other cycloalkenyl, bicycloalkenyl, and tricycloalkenyl groups are known in the art, and such groups are included within the definitions "cycloalkenyl," "bicycloalkenyl" and "tricycloalkenyl" herein.

Unless otherwise indicated, as used herein, the term "aryl" includes an organic radical derived from an aromatic hydrocarbon by removal of one hydrogen, and includes such groups as phenyl, naphthyl, indenyl, indanyl, tetralinyl and fluorenyl. "Aryl" encompasses fused ring groups wherein at least one ring is aromatic.

Unless otherwise indicated, as used herein, the terms "heterocyclic," "heterocycloalkyl," and like terms refer to non-aromatic cyclic groups containing one or more heteroatoms, preferebably from one to four heteroatoms, each selected from O, S and N. "Heterobicycloalkyl" groups are non-aromatic two-ringed cyclic groups, wherein said rings share one or two atoms, and wherein at least one of the rings contains a heteroatom (O, S, or N). Heterobicycloalkyl groups for purposes of the present invention, and unless otherwise indicated, include spiro groups and fused ring groups. The heterocyclic (i.e. heterocycloalkyl, heterobicycloalkyl) groups of the compounds of the subject invention can include O, S(O)$_{zero-2}$, and/or N as heteroatoms, wherein the subscript "zero-2" of S(O)$_{zero-2}$ represents a group of integers consisting of zero, 1 and 2. Thus, S(O)$_{zero-2}$ represents the group consisting of S, S(=O), and S(O)$_2$. In one embodiment, each ring in the heterobicycloalkyl contains up to four heteroatoms (i.e., from zero to four heteroatoms, provided that at least one ring contains at least one heteroatom). The heterocyclic groups, including the heterobicyclic groups, of this invention can also include ring systems substituted with one or more oxo moieties. The heterocyclic groups, including the heterobicyclic groups, may comprise double bonds, e.g., heterocycloalkenyl, heterobicycloalkenyl. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl and 1,4-dioxaspiro[4.5]heptyl.

Unless otherwise indicated, as used herein, "heteroaryl" refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroguinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl and azaindolyl.

As appreciated by the artisan, the use of Formula I is a convenience and the invention; is understood to envision and embrace each and every species hereunder as though individually identified and set forth herein. Thus the present invention contemplates each species separately and any and all combinations and permutations of species falling within Formula I.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

The subject invention also includes all prodrugs of compounds of the Formula I. A prodrug is a compound that may not possess the desired pharmacological activity per se, but can be administered, for example parenterally or orally, to a mammal, thereafter being metabolized in the mammal's body to form a compound that does have the desired pharmacological activity. For example, a prodrug of a compound of the Formula I is metabolized, after administration to a mammal, to a compound of the Formula I. Further, it will be appreciated by those skilled in the art that certain protected derivatives of compounds of the Formula I, that may be made prior to a final deprotection stage, may, in certain instances, be administered to a mammal and thereafter metabolized in the mammal's body to form compounds of the invention that are pharmacologically active. Such derivatives are therefore also "prodrugs" of compounds of the Formula I and are apart of the present invention.

In another aspect, the present invention relates to compounds of the Formula I wherein $R^1$ is halo, $C_1$–$C_4$ alkyl, $C_1$–$C_4$ alkoxy, and wherein said alkyl and alkoxy are optionally substituted with 1 to 3 halo atoms.

In one aspect, the present invention relates to compounds of the Formula I wherein $R^1$ is halo, preferably —Cl, and m is 1.

In another aspect, the present invention relates to compounds of the Formula I wherein $R^2$ is —H;

In another aspect, the present invention relates to compounds of the Formula I wherein $R^3$ is a group of the Formula III, as depicted below

wherein D is —$C_1$–$C_8$ alkyl; and X, Y, Z and B are as defined above, and wherein said X, Y and Z are each optionally independently substituted as defined above.

In another aspect, $R^3$ is a group of the Formula II, as depicted below

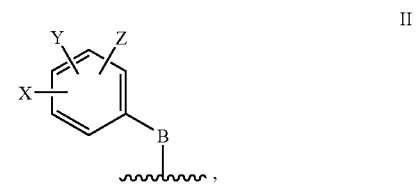

wherein X, Y, Z and B are as defined above, and wherein said X, Y and Z are each optionally independently substituted as defined above.

In another aspect, $R^3$ is a group of the Formula II, as depicted below

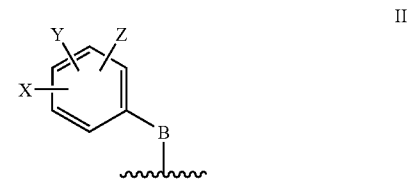

wherein B is $C_1$–$C_4$ alkylene;

X, Y and Z are each independently selected from —H, —$C_1$–$C_8$ alkyl, —$C_2$–$C_8$ alkenyl, —$C_2$–$C_8$ alkoxy —$C_2$–$C_8$ alkenoxy, -halo, —OH, —CN, —NO$_2$, —(CH$_2$)$_q$—NR$^7$R$^8$, —(CH$_2$)$_q$—C(=O)NR$^7$R$^8$, —(CH$_2$)$_q$—C(=O)R$^9$, —(CH$_2$)$_q$—C(=O)OR$^9$, —S(C$_1$–C$_8$ alkyl), —(CH$_2$)$_q$—SO$_2$R$^9$, —(CH$_2$)$_q$—((3–10 membered) heterocycloalkyl), —(CH$_2$)$_q$—(C$_6$–C$_{14}$ aryl), —(CH$_2$)$_q$—((4–10 membered) heteroaryl) and —(CH$_2$)$_q$—(C$_6$–C$_{14}$ aryloxy);

wherein said X, Y and Z are each optionally independently substituted with from one to three substituents independently selected from halo, —OH and —CN; and q is 0, 1 or 2.

In another aspect, $R^3$ is a group of the Formula II, as depicted below

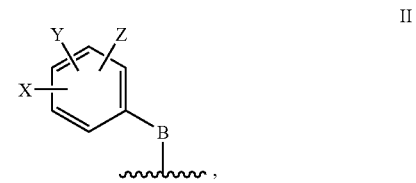

wherein B is methylene; q is 1; and X, Y and Z are as defined immediately above, wherein said X, Y and Z are each optionally independently substituted as defined immediately above.

In another aspect, R³ is a group of the Formula II, as depicted below

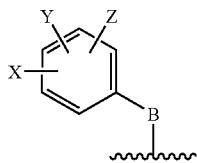

wherein B is C₁–C₈ alkylene;

X, Y and Z are each independently selected from —H, —C₁–C₈ alkyl, —C₂–C₈ alkenyl, —C₁–C₈ alkoxy, —C₂–C₈ alkenoxy, -halo, —OH, —CN, —NO₂, —(CH₂)$_q$—NR⁷R⁸, —(CH₂)$_q$—C(=O)NR⁷R⁸, —(CH₂)$_q$—C(=O)R⁹, —(CH₂)$_q$—C(=O)OR₉, —S(C₁–C₈ alkyl), —(CH₂)$_q$—((3–10 membered) heterocycloalkyl), —(CH₂)$_q$—(C₆–C₁₄ aryl), —(CH₂)$_q$—((4–10 membered) heteroaryl and —(CH₂)$_q$—(C₆–C₁₄ aryloxy);

wherein said alkyl, alkenyl, alkoxy, alkenoxy, —S(C₁–C₈ alkyl), aryl and aryloxy of X, Y and Z are each optionally independently substituted with from one to three substituents independently selected from halo, —OH and —CN; and q is 0, 1 or 2.

In another, aspect, R³ is a group of the Formula II, as depicted below

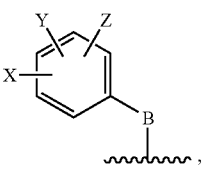

wherein B is C₁–C₈ alkylene; q is 0, 1 or 2; and the aryl of said —(CH2)$_q$—(C₆–C₁₄ aryl) of X, Y and Z is phenyl, the R⁹ of said —(CH₂)$_q$—C(=O)R⁹ and of said —(CH₂)$_q$—SO₂R⁹, both of X, Y and Z, is phenyl, and the aryloxy of said —(CH₂)$_q$—(C₆–C₁₄ aryloxy) of X, Y and Z is phenoxy, wherein said X, Y and Z are each optionally independently substituted as defined immediately above.

In another aspect, R³ is a group of the Formula II, as depicted below

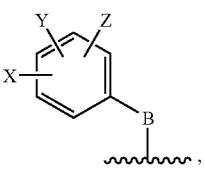

wherein B is C₁–C₈ alkylene; q is 0, 1 or 2; and the heterocycloalkyl of said —(CH₂)$_q$—(3–10membered) heterocycloalkyl of X, Y and Z is selected from pyrrolidinyl and morpholinyl, wherein said X, Y and Z are each optionally independently substituted as defined above.

In another aspect, R³ is a group of the Formula II, as depicted below

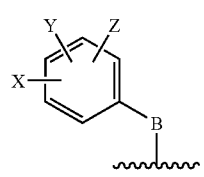

wherein B is —C₁–C₈ alkylene; q is 0, 1 or 2; and the heteroaryl of said —(CH₂)$_q$—(4–10 membered) heteroaryl of X, Y and Z is selected from imidazolyl, thiadiazolyl, oxazolyl, pyrazolyl, isoxazolyl and tetrazolyl, wherein said X, Y and Z are each optionally independently substituted as defined above.

In another aspect, R³ is aryl or benzyl.

Specific embodiments of the present invention include the following compounds of Formula I, all pharmaceutically acceptable salts thereof, complexes thereof, and derivatives thereof that convert into a pharmaceutically active compound upon administration:

4-{[(1—Carbamoyl-2-phenyl-ethyl)-(4-chloro-benzenesulfonyl)-amino]-methyl}-benzoic acid methyl ester;

4-{[(Carbamoyl-phenyl-methyl)-(4-chloro-benzenesulfonyl)-amino]-methyl}-benzoic acid methyl ester;

(R)-2-[(4-Chloro-benzenesulfonyl)-(4-dimethylaminomethyl-benzyl)-amino]-2-phenyl-acetamide;

(R)-2-[(4-Chloro-benzenesulfonyl)-(4-morpholin-4-ylmethyl-benzyl)-amino]-2-phenyl-acetamide;

(R)-2-[Benzyl-(4-chloro-benzenesulfonyl)-amino]-2-phenyl-acetamide;

(R)-2-[(4-Chloro-benzenesulfonyl)-(4-cyano-benzyl)-amino]-2-phenyl-acetamide;

(R)-2-[(4-tert-Butyl-benzyl)-(4-chloro-benzenesulfonyl)-amino]-2-phenyl-acetamide;

(R)-2-[(4-Chloro-benzenesulfonyl)-(3-cyano-benzyl)-amino]-2-phenyl-acetamide;

(R)-2-[(4-Chloro-benzenesulfonyl)-(4-trifluoromethoxybenzyl)-amino]-2-phenyl-acetamide;

(R)-2-[(4-Chloro-benzenesulfonyl)-(4-[1,2,3]thiadiazol-4-yl-benzyl)-amino]-2-phenyl-acetamide;

(R)-2-[(4-Chloro-benzenesulfonyl)-(4-oxazol-2-yl-benzyl)-amino]-2-phenyl-acetamide;

(R)-2-{(4-Chloro-benzenesulfonyl)-[4-(3-methyl-[1,2,4]oxadiazol-5-yl)-benzyl]-amino}-2-phenyl-acetamide;

(R)-2-{(4-Chloro-benzenesulfonyl)-[4-(2-methyl-2H-tetrazol-5-yl)-benzyl]-amino}-2-phenyl-acetamide;

(R)-2-{(4-Chloro-benzenesulfonyl)-[4-(1-hydroxy-1-methyl-ethyl)-benzyl]-amino}-2-phenyl-acetamide;

(R)-2-(2,2-Dimethyl-propylamino)-2-phenyl-acetamide;

(R)-2-[(4-Chloro-benzenesulfonyl)-(2,2-dimethyl-propyl)-amino]-2-phenyl-acetamide;

(R)-2-[(4-Chloro-benzenesulfonyl)-(2-methyl-benzyl)-amino]-2-phenyl-acetamide;

(R)-2-[(4-Chloro-benzenesulfonyl)-(3-methyl-benzyl)-amino]-2-phenyl-acetamide;

(R)-2-[(4-Chloro-benzenesulfonyl)-(3-chloro-benzyl)-amino]-2-phenyl-acetamide;

(R)-2-[(4-Chloro-benzenesulfonyl)-(2-cyano-benzyl)-amino]-2-phenyl-acetamide;

(R)-2-[(4-Chloro-benzenesulfonyl)-(3-fluoro-benzyl)-amino]-2-phenyl-acetamide;
(R)-2-[(4-Chloro-benzenesulfonyl)-(4-fluoro-benzyl)-amino]-2-phenyl-acetamide;
(R)-2-[(4-Chloro-benzenesulfonyl)-(4-trifluoromethyl-benzyl)-amino]-2-phenyl-acetamide;
(R)-2-[(4-Chloro-benzenesulfonyl)-(2,4-difluoro-benzyl)-amino]-2-phenyl-acetamide;
(R)-2-[(4-Chloro-benzenesulfonyl)-(3,4-difluoro-benzyl)-amino]-2-phenyl-acetamide;
(R)-2-[(4-Chloro-benzenesulfonyl)-(3-trifluoromethyl-benzyl)-amino]-2-phenyl-acetamide;
(R)-2-[(4-Chloro-benzenesulfonyl)-(2-trifluoromethyl-benzyl)-amino]-2-phenyl-acetamide;
(R)-2-[(4-Chloro-benzenesulfonyl)-(2-chloro-benzyl)-amino]-2-phenyl-acetamide;
(R)-2-[(4-Chloro-benzenesulfonyl)-(2,6-dichloro-benzyl)-amino]-2-phenyl-acetamide;
(R)-2-[(4-Chloro-benzenesulfonyl)-(2-fluoro-benzyl)-amino]-2-phenyl-acetamide;
(R)-2-[(4-Chloro-benzenesulfonyl)-(2,6-difluoro-benzyl)-amino]-2-phenyl-acetamide;
(R)-2-[(4-Chloro-benzenesulfonyl)-(2-chloro-5-trifluoromethyl-benzyl)-amino]-2-phenyl-acetamide;
(R)-2-[(4-Chloro-benzenesulfonyl)-(3-difluoromethoxy-benzyl)-amino]-2-phenyl-acetamide;
(R)-2-[(4-Chloro-benzenesulfonyl)-(3-fluoro-4-trifluoromethyl-benzyl)-amino]-2-phenyl-acetamide;
(R)-2-[(4-Chloro-benzenesulfonyl)-(5-fluoro-2-trifluoromethyl-benzyl)-amino]-2-phenyl-acetamide;
(R)-2-[(4-Chloro-benzenesulfonyl)-(2-trifluoromethoxy-benzyl)-amino]-2-phenyl-acetamide;
(R)-4-{[(Carbamoyl-phenyl-methyl)-(4-chloro-benzenesulfonyl)-amino]-methyl}-3-methoxy-benzoic acid methyl ester;
(R)-2-[Biphenyl-2-ylmethyl-(4-chloro-benzenesulfonyl)-amino]-2-phenyl-acetamide;
(R)-2-[(2-Benzenesulfonylmethyl-benzyl)-(4-chloro-benzenesulfonyl)-amino]-2-phenyl-acetamide;
(R)-2-[(4-Chloro-benzenesulfonyl)-(2,3-difluoro-benzyl)-amino]-2-phenyl-acetamide;
(R)-2-[(4-Chloro-benzenesulfonyl)-(3,5-difluoro-benzyl)-amino]-2-phenyl-acetamide;
(R)-2-[(4-Chloro-benzenesulfonyl)-(2,3,6-trifluoro-benzyl)-amino]-2-phenyl-acetamide;
(R)-3-{[(Carbamoyl-phenyl-methyl)-(4-chloro-benzenesulfonyl)-amino]-methyl}-benzoic acid methyl ester;
(R)-2-[(4-Chloro-benzenesulfonyl)-(3,4-dichloro-benzyl)-amino]-2-phenyl-acetamide;
(R)-2-[(4-Chloro-benzenesulfonyl)-(2-fluoro-3-methyl-benzyl)-amino]-2-phenyl-acetamide;
(R)-2-[(4-Chloro-benzenesulfonyl)-(2,4,5-trifluoro-benzyl)-amino]-2-phenyl-acetamide;
(R)-2-[(4-Chloro-benzenesulfonyl)-(2,4,6-trifluoro-benzyl)-amino]-2-phenyl-acetamide;
(R)-2-[(4-Chloro-benzenesulfonyl)-(2-chloro-4-fluoro-benzyl)-amino]-2-phenyl-acetamide;
(R)-2-{(4-Chloro-benzenesulfonyl)-[3-[(4-fluoro-phenoxy)-benzyl]-amino}-2-phenyl-acetamide;
(R)-2-[(4-Chloro-benzenesulfonyl)-(2'-cyano-biphenyl-4-ylmethyl)-amino]-2-phenyl-acetamide;
(R)-2-[(4-Chloro-benzenesulfonyl)-(4-methyl-benzyl)-amino]-2-phenyl-acetamide;
(R)-2-[(4-Chloro-benzenesulfonyl)-(3-nitro-benzyl)-amino]-2-phenyl-acetamide;
(R)-2-[(4-Chloro-benzenesulfonyl)-(2-methoxy-5-nitro-benzyl)-amino]-2-phenyl-acetamide;
(R)-2-[(4-Chloro-benzenesulfonyl)-(2-hydroxy-5-nitro-benzyl)-amino]-2-phenyl-acetamide;
(R)-2-[(4-Chloro-benzenesulfonyl)-(4-nitro-benzyl)-amino]-2-phenyl-acetamide;
(R)-2-[(4-Chloro-benzenesulfonyl)-(2,5-difluoro-benzyl)-amino]-2-phenyl-acetamide;
(R)-2-[(4-Bromo-2-fluoro-benzyl)-(4-chloro-benzenesulfonyl)-amino]-2-phenyl-acetamide;
(R)-2-[(4-Chloro-benzenesulfonyl)-(4-fluoro-2-trifluoromethyl-benzyl)-amino]-2-phenyl-acetamide;
(R)-2-[(4-Chloro-benzenesulfonyl)-(3-trifluoromethoxy-benzyl)-amino]-2-phenyl-acetamide;
(R)-2-[(4-Chloro-benzenesulfonyl)-(4,5-dimethoxy-2-nitro-benzyl)-amino]-2-phenyl-acetamide;
(R)-2-[(4-Chloro-benzenesulfonyl)-(3-methoxy-benzyl)-amino]-2-phenyl-acetamide;
(R)-2-[(4-Chloro-benzenesulfonyl)-(3,5-dimethoxy-benzyl)-amino]-2-phenyl-acetamide;
(R)-2-[(4-Chloro-benzenesulfonyl)-(4-trifluoromethyl-sulfanyl-benzyl)-amino]-2-phenyl-acetamide;
(R)-2-[(4-Benzoyl-benzyl)-(4-chloro-benzenesulfonyl)-amino]-2-phenyl-acetamide;
(R)-2-[(4-Butoxy-2-trifluoromethyl-quinolin-6-ylmethyl)-(4-chloro-benzenesulfonyl)-amino]-2-phenyl-acetamide;
(R)-2-[(4-Chloro-benzenesulfonyl)-(5,5,8,8-tetramethyl-5,6,7,8-tetrahydro-naphthalen-2-ylmethyl)-amino]-2-phenyl-acetamide;
(R)-2-[(3-Benzyloxy-benzyl)-(4-chloro-benzenesulfonyl)-amino]-2-phenyl-acetamide;
(R)-2-[(4-Chloro-benzenesulfonyl)-(4-pyrazol-1-yl-benzyl)-amino]-2-phenyl-acetamide;
(R)-2-[(4-Chloro-benzenesulfonyl)-(4-ethyl-benzyl)-amino]-2-phenyl-acetamide;
(R)-N-Butyl-4-{[(carbamoyl-phenyl-methyl)-(4-chloro-benzenesulfonyl)-amino]-methyl}-benzamide;
(R)-4-{[(Carbamoyl-phenyl-methyl)-(4-chloro-benzenesulfonyl)-amino]-methyl}-N-methyl-benzamide;
(R)-(4-{[(Carbamoyl-phenyl-methyl)-(4-chloro-benzenesulfonyl)-amino]-methyl}-phenyl)-acetic acid 2-oxo-2-phenyl-ethyl ester;
(R)-2-[(3,5-Bis-trifluoromethyl-benzyl)-(4-chloro-benzenesulfonyl)-amino]-2-phenyl-acetamide;
(R)-2-[(4-Benzoyl-benzyl)-(4-chloro-benzenesulfonyl)-amino]-2-phenyl-acetamide;
(R)-2-{(4-Chloro-benzenesulfonyl)-[3-(2-fluoro-phenoxy)-benzyl]-amino}-2-phenyl-acetamide;
(R)-2-[(4-Chloro-benzenesulfonyl)-(4-chloro-benzyl)-amino]-2-phenyl-acetamide;
(R)-2-[(4-Chloro-benzenesulfonyl)-(3,5-dimethyl-benzyl)-amino]-2-phenyl-acetamide; and
(R)-2-[(4-Chloro-benzenesulfonyl)-(4-fluoro-3-trifluoromethyl-benzyl)-amino]-2-phenyl-acetamide.

Specific embodiments of the present invention also include the following compounds of Formula I, all pharmaceutically acceptable salts thereof, complexes thereof, and derivatives thereof that convert into a pharmaceutically active compound upon administration:
(R)-2-[(4-Chloro-benzenesulfonyl)-(4-morpholin-4-ylmethyl-benzyl)-amino]-N-methyl-2-phenyl-acetamide;
(R)-2-[(4-Chloro-benzenesulfonyl)-(4-morpholin-4-ylmethyl-benzyl)-amino]-N-ethyl-2-phenyl-acetamide;
(R)-4-{[(4-Chloro-benzenesulfonyl)-(methylcarbamoyl-phenyl-m ethyl)-amino]-methyl}-N-methyl-benzamide;
(R)-4-{[(4-Chloro-benzenesulfonyl)-(ethylcarbamoyl-phenyl-methyl)-amino]-methyl}-N-methyl-benzamide;

(R)-2-[(4-Bromo-2-fluoro-benzyl)-(4-chloro-benzene-sulfonyl)-amino]-N-methyl-2-phenyl-acetamide;
(R)-2-[(4-Bromo-2-fluoro-benzyl)-(4-chloro-benzene-sulfonyl)-amino]-N-ethyl-2-phenyl-acetamide;
(R)-2-[(4-Chloro-benzenesulfonyl)-(4-oxazol-2-yl-benzyl)-amino]-N-methyl-2-phenyl-acetamide;
(R)-2-[(4-Chloro-benzenesulfonyl)-(4-oxazol-2-yl-benzyl)-amino]-N-ethyl-2-phenyl-acetamide;
(R)-2-[(4-Chloro-benzenesulfonyl)-(4-chloro-2-fluoro-benzyl)-amino]-2-phenyl-acetamide;
(R)-2-[(4-Chloro-benzenesulfonyl)-(4-chloro-2-fluoro-benzyl)-amino]-N-methyl-2-phenyl-acetamide;
(R)-2-[(4-Chloro-benzenesulfonyl)-(4-chloro-2-fluoro-benzyl)-amino]-N-ethyl-2-phenyl-acetamide;.
(R)-4-{[(Carbamoyl-phenyl-methyl)-(4-trifluoromethoxy-benzenesulfonyl)-amino]-methyl}-benzoic acid methyl ester;
(R)-4-{[(Carbamoyl-phenyl-methyl)-(4-cyano-benzenesulfonyl)-amino]-methyl}-benzoic acid methyl ester;
(R)-4-{[(Carbamoyl-phenyl-methyl)-(3-chloro-4-methylbenzenesulfonyl)-amino]-methyl}-benzoic acid methyl ester;
(R)-4-{[(Carbamoyl-phenyl-methyl)-(3-fluoro-benzenesulfonyl)-amino]-methyl}-benzoic acid methyl ester;
(R)-4-{[(Carbamoyl-phenyl-methyl)-(2,3,4-trifluoro-benzenesulfonyl)-amino]-methyl}-benzoic acid methyl ester;
(R)-4-{[(Carbamoyl-phenyl-methyl)-(3,4-difluoro-benzenesulfonyl)-amino]-methyl}-benzoic acid methyl ester;
(R)-4-{[(3-Bromo-benzenesulfonyl)-(carbamoyl-phenyl-methyl)-amino]-methyl}-benzoic acid methyl ester;
(R)-4-{[(Carbamoyl-phenyl-methyl)-(toluene-4-sulfonyl)-amino]-methyl}-benzoic acid methyl ester;
(R)-4-{[Benzenesulfonyl-(carbamoyl-phenyl-methyl)-amino]-methyl}-benzoic acid methyl ester;
(R)-4-{[(4-Bromo-benzenesulfonyl)-(carbamoyl-phenyl-methyl)-amino]-methyl}-benzoic acid methyl ester;
(R)-4-{[(Carbamoyl-phenyl-methyl)-(3-trifluoromethyl-benzenesulfonyl)-amino]-methyl}-benzoic acid methyl ester;
(R)-4-{[(Carbamoyl-phenyl-methyl)-(4-fluoro-benzenesulfonyl)-amino]-methyl}-benzoic acid methyl ester;
(R)-4-{[(Carbamoyl-phenyl-methyl)-(4-methoxy-benzenesulfonyl)-amino]-methyl}-benzoic acid methyl ester;
(R)-4-{[(Carbamoyl-phenyl-methyl)-(toluene-3-sulfonyl)-amino]-methyl}-benzoic acid methyl ester;
R)-4-{[(Carbamoyl-phenyl-methyl)-(2-chloro-benzenesulfonyl)-amino]-methyl}-benzoic acid methyl ester;
(R)-4-{[(Carbamoyl-phenyl-methyl)-(3-chloro-4-fluoro-benzenesulfonyl)-amino]-methyl}-benzoic acid methyl ester;
(R)-4-{[(Carbamoyl-phenyl-methyl)-(2,4-difluoro-benzenesulfonyl)-amino]-methyl}-benzoic acid methyl ester;
(R)-4-{[(Carbamoyl-phenyl-methyl)-(3,5-difluoro-benzenesulfonyl)-amino]-methyl}-benzoic acid methyl ester;
(R)-4-{[(Carbamoyl-phenyl-methyl)-(4-chloro-3-nitro-benzenesulfonyl)-amino]-methyl}-benzoic acid methyl ester;
(R)-4-{[(Carbamoyl-phenyl-methyl)-(5-fluoro-2-methyl-benzenesulfonyl)-amino]-methyl}-benzoic acid methyl ester;
(R)-4-{[(Carbamoyl-phenyl-methyl)-(2,3-dichloro-benzenesulfonyl)-amino]-methyl}-benzoic acid methyl ester;
(R)-4-{[(4-Bromo-2-methyl-benzenesulfonyl)-(carbamoyl-phenyl-methyl)-amino]-methyl}-benzoic acid methyl ester;
(R)-4-{[(Carbamoyl-phenyl-methyl)-(2-trifluoromethoxy-benzenesulfonyl)-amino]-methyl}-benzoic acid methyl ester;
(R)-4-{[(Carbamoyl-phenyl-methyl)-(3,4-dimethoxy-benzenesulfonyl)-amino]-methyl}-benzoic acid methyl ester;
(R)-4-{[(Carbamoyl-phenyl-methyl)-(4-chloro-2,5-dimethyl-benzenesulfonyl)-amino]-methyl}-benzoic acid methyl ester;
(R)-4-{[(Carbamoyl-phenyl-methyl)-(4-isopropyl-benzenesulfonyl)-amino]-methyl}-benzoic acid methyl ester;
(R)-4-{[(Carbamoyl-phenyl-methyl)-(4-propyl-benzenesulfonyl)-amino]-methyl}-benzoic acid methyl ester; and
(R)-4-{[(Carbamoyl-phenyl-methyl)-(3-nitro-benzenesulfonyl)-amino]-methyl}-benzoic acid methyl ester.

As indicated, so-called 'prodrugs' of the compounds of Formula I are also within the scope of the invention. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Some examples of prodrugs in accordance with the invention include, but are not limited to, (i) where the compound of Formula I contains a carboxylic acid functionality (—COOH), an ester thereof, for example, a compound wherein the hydrogen of the carboxylic acid functionality of the compound of Formula (I) is replaced by $(C_1-C_8)$alkyl;

(ii) where the compound of Formula I contains an alcohol functionality (—OH), an ether thereof, for example, a compound wherein the hydrogen of the alcohol functionality of the compound of Formula I is replaced by $(C_1-C_6)$alkanoyloxymethyl; and (iii) where the compound of Formula I contains a primary or secondary amino functionality (—NH$_2$ or —NHR where R≠H), an amide thereof, for example, a compound wherein, as the case may be, one or both hydrogens of the amino functionality of the compound of Formula I is/are replaced by $(C_1-C_{10})$alkanoyl.

Further examples of replacement groups in accordance with the foregoing examples and examples of other prodrug types may be found in the aforementioned references.

Moreover, certain compounds of Formula I may themselves act as prodrugs of other compounds of Formula I.

Also included within the scope of the invention are metabolites of compounds of Formula I, that is, compounds formed in vivo upon administration of the drug. Some examples of metabolites in accordance with the invention include, but are not limited to, (i) where the compound of Formula I contains a methyl group, an hydroxymethyl derivative thereof (—CH$_3$-→—CH$_2$OH):

(ii) where the compound of Formula I contains an alkoxy group, an hydroxy derivative thereof (—OR-→—OH);

(iii) where the compound of Formula I contains a tertiary amino group, a secondary amino derivative thereof (—NR$^1$R$^2$-→—NHR$^1$ or —NHR$^2$);

(iv) where the compound of Formula I contains a secondary amino group, a primary derivative thereof (—NHR$^1$-→—NH$_2$);

(v) where the compound of Formula I contains a phenyl moiety, a phenol derivative thereof (—Ph-→—PhOH); and (vi) where the compound of Formula I contains an amide group, a carboxylic acid derivative thereof (—CONH$_2$-→COOH).

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The present invention includes all pharmaceutically acceptable isotopically-labelled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula I, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

Also within the scope of the invention are intermediate compounds of Formula II as hereinbefore defined, all salts, solvates and complexes thereof and all solvates and complexes of salts thereof as defined hereinbefore for compounds of Formula I. The invention includes all polymorphs of the aforementioned species and crystal habits thereof.

When preparing compounds of Formula I in accordance with the invention, it is open to a person skilled in the art to routinely select the form of compound of Formula II which provides the best combination of features for this purpose. Such features include, but are not limited to, the melting point, solubility, processability and yield of the intermediate form and the resulting ease with which the product may be purified on isolation.

Compounds of the Formula I of this invention, and their pharmaceutically acceptable salts, have useful pharmaceutical and medicinal properties. The compounds of Formula I, and their pharmaceutically acceptable salts inhibit the production of Aβ-peptide (thus, gamma-secretase activity) in mammals, including humans. Compounds of the Formula I, and their pharmaceutically acceptable salts, are therefore able to function as therapeutic agents in the treatment of the neurodegenerative and/or neurological disorders and diseases representatively enumerated below, for example Alzheimer's disease, in an afflicted mammal, including a human.

The present invention also relates to a pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising an amount of a compound of the Formula I, or a pharmaceutically acceptable salt thereof, that is effective in inhibiting Aβ-peptide production, and a pharmaceutically acceptable carrier.

The present invention also relates to a pharmaceutical composition for treating a disease or condition selected from the group consisting of Alzheimer's disease and Down's Syndrome in a mammal, including a human, comprising an amount of a compound of the Formula I, or a pharmaceutically acceptable salt thereof, that is effective in inhibiting Aβ-peptide production, and a pharmaceutically acceptable carrier.

The present invention also relates to a pharmaceutical composition for treating a disease or a condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising an amount of a compound of the Formula I, or a pharmaceutically acceptable salt thereof, that is effective in treating such disease or condition, and a pharmaceutically acceptable carrier.

The present invention also relates to a pharmaceutical composition for treating a disease or a condition selected from the group consisting of Alzheimer's disease and Down's Syndrome in a mammal, including a human, comprising an amount of a compound of the Formula I, or a pharmaceutically acceptable salt thereof, that is effective in treating such disease or condition, and a pharmaceutically acceptable carrier.

The present invention also relates to a method of treating a disease or condition selected from Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising administering to said mammal an amount of a compound of the Formula I, or a pharmaceutically acceptable salt thereof, that is effective in inhibiting Aβ-production.

The present invention also relates to a method of treating a disease or condition selected from Alzheimer's disease and Down's Syndrome in a mammal, including a human, comprising administering to said mammal an amount of a compound of the Formula I, or a pharmaceutically acceptable salt thereof, that is effective in inhibiting Aβ-production.

The present invention also relates to a method of treating a disease or condition selected from Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising administering to said mammal an amount of a compound of the Formula I, or a pharmaceutically acceptable salt thereof, that is effective in treating such condition.

The present invention also relates to a method of treating a disease or condition selected from Alzheimer's disease and Down's Syndrome in a mammal, including a human, comprising administering to said mammal an amount of a compound of the Formula I, or a pharmaceutically acceptable salt thereof, that is effective in treating such condition.

The compounds of Formula I may be used alone or used in combination with any other drug, including, but not limited to, any memory enhancement agent, e.g., Aricept™ and/or Namenda™, antidepressant agent, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertension agent, e.g., Norvasc™, Caduet™, etc. Accordingly, the present invention also relates to the following pharmaceutical compositions and methods of treatment comprising a compound of the Formula I in combination with other drugs, such as those of the type described above.

The present invention also relates to a pharmaceutical composition for treating a disease or condition associated with Aβ-peptide production in a mammal, including a human, comprising (a) a compound of the Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; and (c) a pharmaceutically acceptable carrier; wherein the active agents "a" and "b" above are present in amounts that render the composition effective in treating such disease or condition.

The present invention also relates to a pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome, in a mammal, including a human, comprising (a) a compound of the Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases-HDL), e.g., Lipitor™, Caduet™, etc., Histamine (H2) antagonist, e.g., Cimetadine™, and anti-hypertensive agent, e.g., Norvasc™, Caduet™, etc.; and (c) a pharmaceutically acceptable carrier; wherein the active agents "a" and "b" above are present in amounts that render the composition effective in treating such disease or condition.

The present invention also relates to a pharmaceutical composition for treating a disease or condition selected from the group consisting of Alzheimer's disease and Down's Syndrome, in a mammal, including a human, comprising (a) a compound of the Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; and (c) a pharmaceutically acceptable carrier; wherein the active agents "a" and "b" above are present in amounts that render the composition effective in treating such disease or condition.

The present invention also relates to a method of treating a disease or condition associated with Aβ-peptide production in a mammal, including a human, comprising administering to said mammal (a) a compound of the Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; wherein the active agents "a" and "b" above are present in amounts that render the composition effective in treating such disease or condition.

The present invention also relates to a method of treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome, in a mammal, including a human, comprising administering to said mammal (a) a compound of the Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; wherein the active agents "a" and "b" above are present in amounts that render the composition effective in treating such disease or condition.

The present invention also relates to a method of treating a disease or condition selected from the group consisting of Alzheimer's disease and Down's Syndrome, in a mammal, including a human, comprising administering to said mammal (a) a compound of the Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Novasc™; Caduet™, etc.; wherein the active agents "a" and "b" above are present in amounts that render the composition effective in treating such disease or condition.

Compounds of the Formula I, or any of the combinations described in the immediately preceding paragraphs, may optionally be used in conjunction with a known P-glycoprotein inhibitor, such as verapamil.

References herein to diseases and conditions "associated with Aβ-peptide production" relate to diseases or conditions that are caused, at least in part, by Aβ-peptide and/or the production thereof. Thus, Aβ-peptide is a contributing factor, but not necessarily the only contributing factor, to "a disease or condition associated with Aβ-peptide production." The compounds of Formula I, and their pharmaceutically acceptable salts may also be used to modulate or inhibit the Notch signaling pathway in organisms, including humans. The Notch signaling pathway is an evolutionarily conserved mechanism utilized by organisms, ranging from worms through humans, to regulate fate determination of various cell lineages. Notch belongs to the family of epidermal growth factor-like homeotic genes, which encode transmembrane proteins with variable numbers of epidermal growth factor-like repeats in the extracellular domain. There is increasing evidence for a role of the Notch pathway in human disease. All of the components of the pathway have yet to be identified, but among those identified to date, mutations that affect their interaction with each other can lead to a variety of syndromes and pathological conditions.

For example, Notch signaling is typically associated with cell fate decision. The finding that Notch activation stimulates capillary outgrowth suggests that Notch receptors must be activated to allow this process to occur. Therefore, Notch modulation provides a method for regulating angiogenesis. Specifically, modulation of Notch signaling can be used to modulate angiogenesis (e.g., by blocking Notch signaling to block angiogenesis). This inhibition of angiogenesis in vivo can be used as a therapeutic means to treat a variety of diseases, including but not limited to cancer, diabetic retinopathy, rheumatoid arthritis, psoriasis, inflammatory bowel disease and arteriosclerosis.

The Notch pathway is also implicated in the development and maturation of T cells, as described in Radtke, F. et al., Immunity 10:547–558, 1999. The compounds of Formula I, and their pharmaceutically acceptable salts are therefore useful candidates for modulating the immune system, including the treatment of inflammation, asthma, graft rejection, graft versus host disease, autoimmune disease and transplant rejection.

In addition,. a number of studies published between 2002 and 2004 have provided convincing evidence that Notch signaling is frequently elevated in a variety of human tumors (including, but not limited to breast, prostate, pancreas and T-cell acute lymphoblastic leukemia). One key study provides a strong genetic link to Notch's role in important tumor types. Specifically, Weijzen et al. demonstrated that Notch signaling maintains the neoplastic phenotype in human Ras-transformed cells. Weijzen et al. (2002) *Nature Med* 8: 979. Because 30% of human malignancies may carry activating mutations in at least one of the three isoforms of Ras, this finding raises the possibility that Notch inhibitors would be a powerful addition to anti-cancer therapy. Another study's findings support a central role for aberrant Notch signaling in the pathogenesis of human T cell acute lymphoblastic leukemia/lymphoma. Pear et al., *Current Opinion in Hematology* (2004), 11(6), 426–433.

Accordingly, the compounds of Formula I, and their pharmaceutically acceptable salts, may be used for treating a disease or condition selected from the group consisting of cancer, arteriosclerosis, diabetic retinopathy, rheumatoid arthritis, psoriasis, inflammatory bowel disease inflammation, asthma, graft rejection, graft versus host disease, autoimmune disease and transplant rejection.

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refermto the act of treating, as "treating" is defined above.

DETAILED DESCRIPTION OF THE INVENTION

Compounds of the Formula I, and their pharmaceutically acceptable salts, may be prepared as described in the following reaction Schemes and discussion. Unless otherwise indicated, as referred to in the reaction schemes and discussion that follow, $R^1$, $R^2$, $R^3$, $R^5$, $R^6$, $R^7$, $R^8$, $R^9$, A, m, n and q are as defined above.

The compounds of Formula I may have asymmetric carbon atoms and may therefore exist as racemic mixtures, diastereoisomers, or as individual optical isomers.

Separation of a mixture of isomers of compounds of Formula I into single isomers may be accomplished according to conventional methods known in the art.

The compounds of the Formula I may be prepared by the methods described below, together with synthetic methods known in the art of organic chemistry, or modifications and derivatisations that are familiar to those of ordinary skill in the art. Preferred methods include, but are not limited to, those described below.

The reactions described below are performed in solvents that are appropriate to the reagents and materials employed and that are suitable for use in the reactions described. In the description of the synthetic methods described below, it is also to be understood that all reaction conditions, whether actual or proposed, including choice of solvent, reaction temperature, reaction duration time, reaction pressure, and other reaction conditions (such as anhydrous conditions, under argon, under nitrogen, etc.), and work up procedures, are those conditions that are standard for that reaction, as would be readily recognized by one of skill in the art. Alternate methods may also be used.

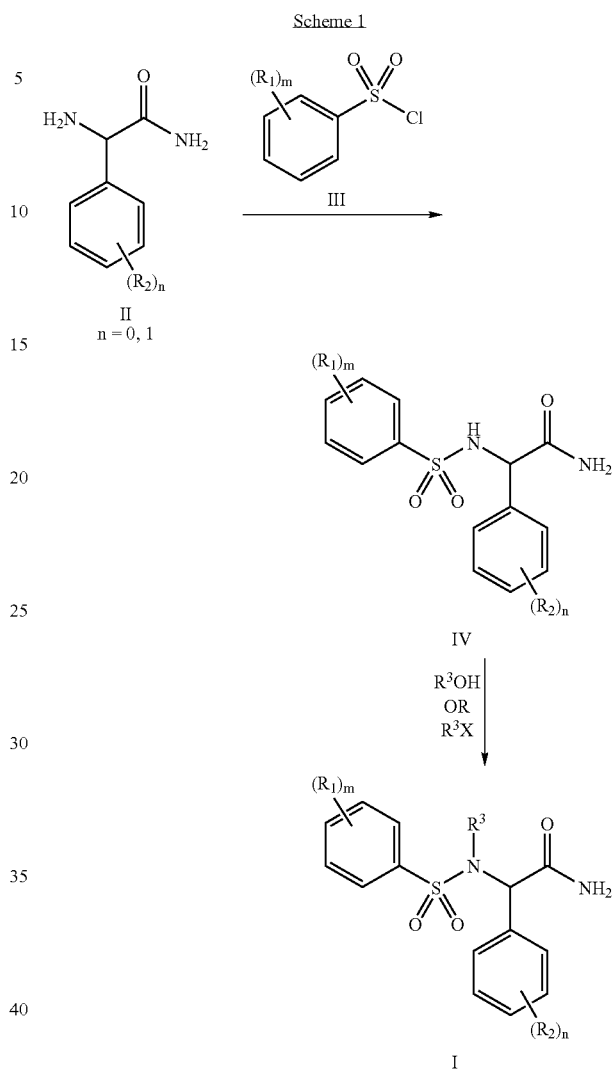

Scheme 1 illustrates methods suitable for preparing sulfonamide compounds of formula I. The amide derivatives II are available commercially as racemic mixtures or single enantiomers or prepared by methods known in the chemical literature such as *Chem. Ber.* 1939; 72, 1291; *J. Chem. Soc.* 1911, 99, 323; *J. Org. Chem.,* 1962, 27, 798; *J. Org. Chem.* 1962, 27, 798; *Bull. Soc. Chim. Belg.* 1997, 106, 67; *Chem. Pharm. Bull.* 2000, 48, 1586; *J. Org. Chem.* 2002, 67, 3687; *J. Med. Chem.* 2002, 45, 5471; *Collect. Czech. Chem. Commun.* 1995, 60, 150; *J. Chem. Soc. C.* 1968; 531; *Tetrahedron Lett.* 1992, 33, 6007. The amide derivatives II are reacted with a sulfonyl chloride III in a solvent such as methylene chloride, dichloroethane, toluene, benzene, or ether in which methylene chloride is preferred at a temperature from −50° C. to 50° C. in which −10° C. to 23° C. is preferred to afford sulfonamides IV. The sulfonamides IV are treated with a base such as potassium carbonate, sodium carbonate, alkoxide, alkyllithiate in which potassium carbonate is preferred and $R^3$—X where X is defined as bromide, iodide, fluoride, chloride, alkylsulfonate or arylsulfonate at a temperature from 23° C. to 100° C. where 40° C. to 60° C. is preferred in a solvent such as methylene chloride, dimethylsulfoxide, dimethylformamide, tetrahydrofuran, acetonitrile, or toluene where dimethylformamide is preferred affords compounds of Formula I. Alternatively, sulfonamide IV is treated with triarylphospine such as triphenylphospine, a dialkylazodicaroxylate, and $R^3$—OH in a solvent such as tetrahydrofuran, methylene chloride, or toluene wherein tetrahydrofuran is preferred at a temperature from 0° C. to 100° C. wherein 23° C. c to 50° C. is preferred affords compounds of Formula I.

ethylformamide, dimethylsulfoxide (DMSO), N-methyl pyrrolidinone (NMP), or xylene, at a temperature of from about −30° C. to about room temperature followed by the addition of an amine at a temperature from about 0° C. to 100° C., preferably 20° C. In step 3, the ester VI can be converted to the amide VIII using methods well known in the chemical literature such as treatment with ammonia in an alcoholic solvent such as methanol with heating from 50° C. to 75° C.

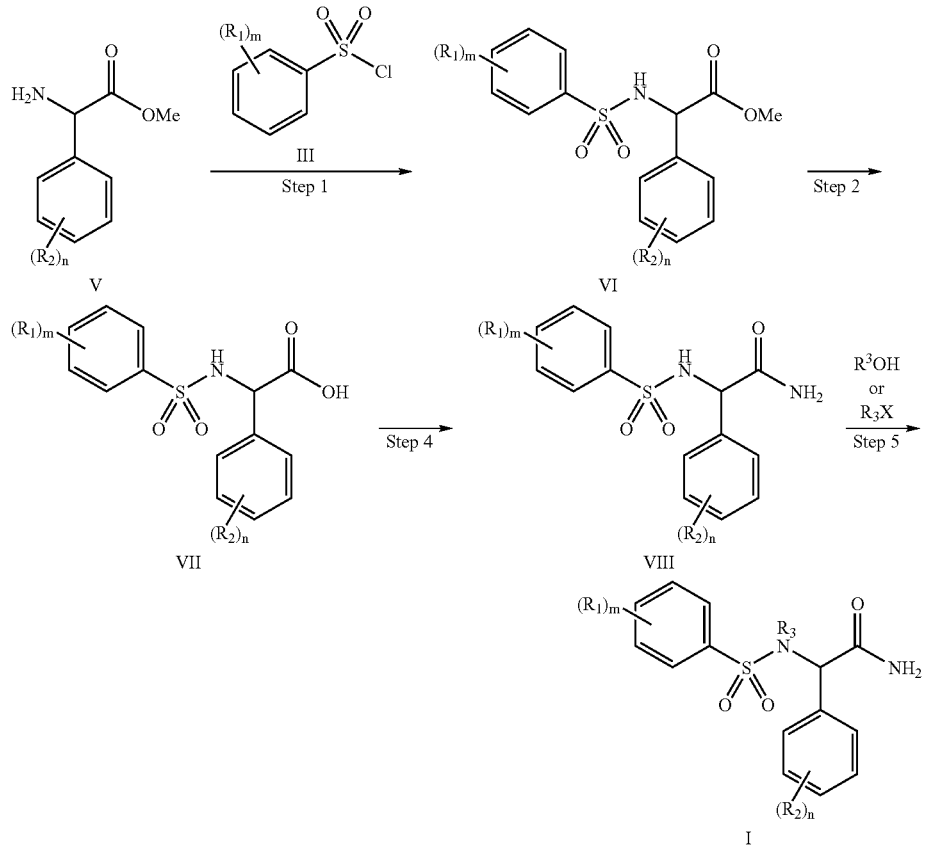

Scheme 2 illustrates methods suitable for preparing sulfonamide compounds of formula I. The amide derivatives V are available commercially as racemic mixtures or single enantiomers or prepared by methods previously reported in the chemical literature. In step 1, the amide derivatives V are reacted with a sulfonyl chloride III in a solvent such as methylene chloride, dichloroethane, toluene, benzene, or ether in which methylene chloride is preferred at a temperature from −50° C. to 50° C. in which −10° C. to 23° C. is preferred affords sulfonamides VI. In step 2, the ester is hydrolyzed using sodium or lithium hydroxide to afford the acid VII. In step 4, the acid is converted to amide VII by converting the acid into a leaving group by reaction with oxalyl chloride, thionyl chloride or a mixed anhydride method, using an alkyl chloroformate, such as $C_1$–$C_4$ alkyl chloroformate, in the presence of a base such as triethylamine, N,N-diisopropylethylamine, pyridine, or dimethylaminopyridine, in a suitable solvent such as, for example, methylene chloride, chloroform, tetrahydrofuran (THF), toluene, diethyl ether, acetonitrile, 1,4-dioxane, N,N-dimto afford the amides VIII. Alternatively, ester VI can be converted to the amide VIII in the presence of an amine which has been treated with trialkylaluminium preferably trimethylaluminum in an appropriate solvent such as methylene chloride, THF, dioxane, toluene, etc., at an appropriate temperature, such as from about room temperature to about reflux, or in a sealed reactor (such as sealed tube or inscrewed vials). The sulfonamides VIII are treated with a base such as potassium carbonate, sodium carbonate, alkoxide, alkyllithiate in which potassium carbonate is preferred and $R^3$—X where X is defined as bromide, iodide, fluoride, chloride, alkylsulfonate or arylsulfonate at a temperature from 23° C. to 100° C. where 40° C. to 60° C. is preferred in a solvent such as methylene chloride, dimethylsulfoxide, dimethylformamide, tetrahydrofuran, acetonitrile, toluene where dimethylformamide is preferred affords compounds of Formula I. Alternatively, sulfonamide VIII is treated with triarylphospine such as triphenylphospine, a dialkylazodicaroxylate, and $R^3$—OH in a solvent such as tetrahydrofuran, methylene chloride, toluene wherein tetrahydrofuran is

Scheme 3

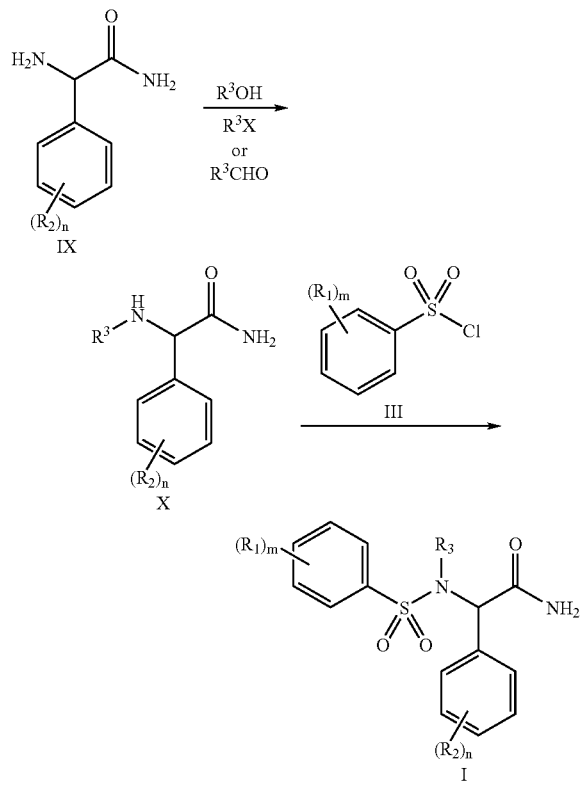

Scheme 3 illustrates methods suitable for preparing sulfonamide compounds of formula I. The amide derivatives IX are available commercially as racemic mixtures or single enantiomers or prepared by methods previously reported in the chemical literature from amines II. The amines IX are treated with a base such as potassium carbonate, sodium carbonate, alkoxide, alkyllithiate in which potassium carbonate is preferred and $R^3$—X where X is defined as bromide, iodide, fluoride, chloride, alkylsulfonate or arylsulfonate at a temperature from 23° C. to 100° C. where 40° C. to 60° C. is preferred in a solvent such as methylene chloride, dimethylsulfoxide, dimethylformamide, tetrahydrofuran, acetonitrile, toluene where dimethylformamide is preferred affords compounds of Formula X. Alternatively, amines IX is treated with triarylphospine such as triphenylphospine, a dialkylazodicaroxylate, and $R^3$—OH in a solvent such as tetrahydrofuran, methlyene chloride, toluene wherein tetrahydrofuran is preferred at a temperature from 0° C. to 100° C. wherein 23° C. c to 50° C. is preferred affords compounds of Formula X. Alternatively, amine IX is converted to X using a well-established reductive amination method by reacting amine IX with a ketone or aldehyde with or without acid catalyst/ammonium acetate/dry agents (such as anhydrous $Na_2SO_4$ or $MgSO_4$), and a reducing agent, such as sodium triacetoxyborohydride, sodium cyanoborohydride, sodium borohydride, or the corresponding polymer bound-$NaBH_4$, polymer bound-$NaBH_3CN$, or polymer bound-$NaB(OAc)_3H$, or any reducing agent (e.g., hydrogenation) that is known in the literature for reducing an imine bond to an amine, in an appropriate solvent, such as dichloroethane, chloroform, THF, MeOH, ethanol, isopropanol, t-butanol or toluene, at a temperature from about room temperature to about reflux, preferably from about room temperature to about 65° C. The derivatives X are reacted with a sulfonyl chloride III in a solvent such as methylene chloride, dichloroethane, toluene, benzene, ether, dimethylformamide in which dichloroethane is preferred at a temperature from −50° C. to 100° C. in which 20° C. to 80° C. is preferred affords compounds of Formula I.

Scheme 4

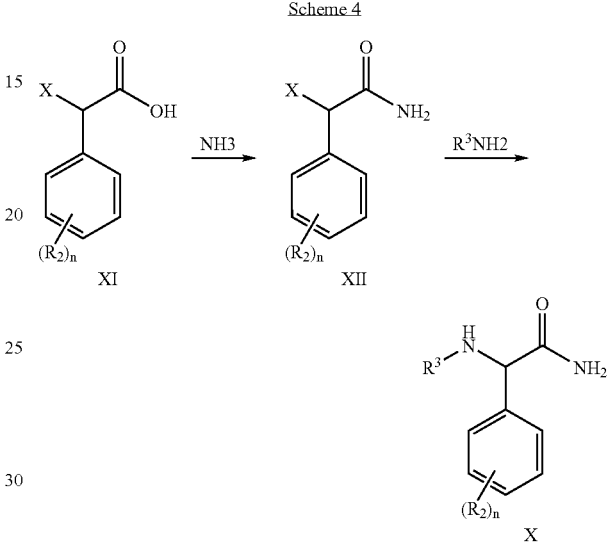

Scheme 4 illustrates methods suitable for preparing intermediate X which affords sulfonamide compounds of formula I using methods described above. The acid derivatives XI are available commercially as racemic mixtures or single enantiomers or are prepared by methods well known in the chemical literature. The amides XII are formed from acid XI using methods well known in the literature (Cabre, J. Synthesis, 5; 1984, 413–417). Treatment of XII (where X is halide or aryl sulfonate) with an appropriate amine ($R^3NH_2$) at a temperature from 23° C. to 100° C. where 60° C. to 80° C. is preferred neat or in a solvent such as methylene chloride, dimethylsulfoxide, dimethylformamide, tetrahydrofuran, acetonitrile, toluene where neat is preferred affords compounds of Formula X. Alternatively, treatment of XII (where X is OH) with a triarylphospine such as triphenylphospine, a dialkylazodicaroxylate, and $R^3$—$NH_2$ in a solvent such as tetrahydrofuran, methylene chloride, toluene wherein tetrahydrofuran is preferred at a temperature from 0° C. to 100° C. wherein 23° C. to 50° C. is preferred affords compounds of Formula X.

The starting materials used in the procedures of the Schemes described above, the syntheses of which are not described above, are either commercially available, known in the art or readily obtainable from known compounds using methods that will be apparent to those skilled in the art.

The compounds of Formula I, and the intermediates shown in the above reaction schemes, may be isolated and purified by conventional procedures, such as recrystallization or chromatographic separation, such as on silica gel, either with an ethyl acetate/hexane elution gradient, a methylene chloride/methanol elution gradient, or a chloroform/ methanol elution gradient. Alternatively, a reverse phase preparative HPLC or chiral HPLC separation technique may be used.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

A compound of the Formula I of the present invention, or pharmaceutically acceptable salt thereof, may be administered to mammals via either the oral, parenteral (such as subcutaneous, intravenous, intramuscular, intrasternal and infusion techniques), rectal, intranasal, topical or transdermal (e.g., through the use of a patch) routes. In general, these compounds are most desirably administered in doses ranging from about 0.1 mg to about 1000 mg per day, in single or divided doses (i.e., from 1 to 4 doses per day), although variations will necessarily occur depending upon the species, weight, age and condition of the subject being treated, as well as the particular route of administration chosen. However, a dosage level that is in the range of about 0.1 mg/kg to about 5 gm/kg body weight per day, preferably from about 0.1 mg/kg to about 100 mg/kg body weight per day, is most desirably employed. Nevertheless, variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such higher dosage levels are first divided into several small doses for administration throughout the day. Varations based on the aforementioned dosage range may be made by a physicain of ordinary skill.

A compound of the Formula I of the present invention may be administered alone or in combination with pharmaceutically acceptable carriers or diluents by either of the routes previously indicated, and such administration may be carried out in single or multiple doses. Suitable pharmaceutical carriers include solid diluents or fillers, sterile aqueous media and various non-toxic organic solvents, etc. The pharmaceutical compositions formed by combining a compound of the Formula I, or a pharmaceutically acceptable salt thereof, with a pharmaceutically acceptable inert carrier, can then be readily administered in a variety of dosage forms such as tablets, capsules, lozenges, troches, hard candies, powders, sprays, creams, salves, suppositories, jellies, gels, pastes, lotions, ointments, aqueous suspensions, injectable solutions, elixirs, syrups, and the like. Moreover, oral pharmaceutical compositions may be suitably sweetened and/or flavored.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), methylcellulose, alginic acid and certain complex silicates, together with granulation binders such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in gelatin capsules. Preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions containing a compound of the Formula I of the present invention or a pharmaceutically acceptable salt thereof in either sesame or peanut oil, in aqueous propylene glycol or in sterile aqueous solutions may be employed. The aqueous solutions should be suitably buffered (preferably pH greater than 8) if necessary and the liquid diluent first rendered isotonic with sufficient saline or glucose. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The compounds of Formula I of the present invention are useful in inhibiting Aβ-peptide production (thus, gamma-secretase activity) in mammals, and therefore they are able to function as therapeutic agents in the treatment of the aforementioned disorders and diseases in an afflicted mammal.

A specific compound of the Formula I can be determined to inhibit Aβ-peptide production using biological assays known to those of ordinary skill in the art, for example the assays described below.

The activity of compounds of the Formula I of the present invention in inhibiting gamma-secretase activity was determined in a solubilized membrane preparation generally according to the description provided in McLendon et al. Cell-free assays for γ-secretase activity, *The FASEB Journal* (Vol. 14, December 2000, pp. 2383–2386). Using such assay, compounds of the present invention were determined to have an $IC_{50}$ activity for inhibiting gamma-secretase activity of less than about 100 micromolar. Preferred compounds of the invention are compounds that were determined to have an $IC_{50}$ activity for inhibiting gamma-secretase activity of less than about 5 micromolar.

The following Examples illustrate the present invention. It is to be understood, however, that the invention, as fully described herein and as recited in the claims, is not intended to be limited by the details of the following Examples.

EXAMPLES

Preparation 1

2-(4-Chloro-benzenesulfonylamino)-3-phenyl-propionic acid methyl ester

2-Amino-3-phenyl-propionic acid methyl ester is dissolved in 25 mL of methylene chloride and the reaction charged with triethylamine (0.97 mL, 7 mmol) and 4-chlorobenzenesulfonylchloride at 0° C. The reaction is allowed to warm to room temperature (rt) and stirred overnight. The reaction is quenched with sodium bicarbonate, extracted with methylene chloride, dried over sodium sulfate, and concentrated in vacuo. The resultant solid is triturated with 20% ethylacetate/hexanes to provide the title compound. 13C NMR (100 MHz, CDCl3) 39.5, 52.8, 57.1, 127.5, 128.8, 128.9, 129.5, 129.6, 135.1, 138.4, 139.4, 171.5. MS 354.1 m/z (M+1).

(R)-Amino-(4-fluoro-phenyl)-acetic acid methyl ester (R)-Amino-(4-fluoro-phenyl)-acetic acid was treated with HCl gas (8 g) dissolved in methanol at room temperature for 24 hours. The reaction mixture was concentrated and aqueous sodium bicarbonate was added until the pH of the mixture remained basic. The aqueous layer was extracted three times with dichloromethane. The combined extracts were dried ($Na_2SO_4$) and concentrated afford the title compound as an oil. 1HNMR (400 MHz, CDCl3)δ 1.90 (br s, 2H), 3.67 (s, 3H), 4.58 (s, 1H), 7.00 (m, 2H), 7.30 (m, 2H).

Preparation 2

2-(4-Chloro-benzenesulfonylamino)-3-phenyl-propionamide

To 2-(4-Chloro-benzenesulfonylamino)-3-phenyl-propionic acid methyl ester (750 mg) is added 10 mL of a 1.0 M solution of ammonia in methanol. The reaction is heated for 48 h at 65° C., cooled to room temperature, and the solvent removed. The resultant solid is first triturated with ethyl acetate, filtered, and then triturated with methylene chloride to provide the title compound. 1HNMR (400 MHz, CD3OD) 2.70 (dd, 1H, J=14.0 Hz and 9.6 Hz), 3.01 (dd, 1H, J=14.0 Hz and 5.4 Hz), 3.95 (dd, 1H, J=9.0 Hz and 5.0 Hz), 7.05–7.15 (m, 5H), 7.32–7.36 (m, 2H), and 7.53–7.56 (m, 2H). MS 339.1 m/z (M+1).

(R)-2-Amino-2-(4-fluoro-phenyl)-acetamide

The title compound was prepared in the manner of Preparation 2 utilizing (R)-amino-(4-fluoro-phenyl)-acetic acid methyl ester to yield the desired product. 1HNMR (400 MHz, CDCl3)δ 4.30 (s, 1H), 5.54 (br s, 1H), 6.91 (br s, 1H), 7.05 (m, 2H), 7.40 (m, 2H).

Example 1

4-{[(1—Carbamoyl-2-phenyl-ethyl)-(4-chloro-benzenesulfonyl)-amino]-methyl}-benzoic acid methyl ester To a solution of triphenylphosphine (110 mmg, 0.4 mmol) in 0.7 mL of tetrahydrofuran is added diisopropyl azodicarboxylate (0.08 mL, 0.4 mmol) and the reaction stirred for 30 min. To the reaction is added 0.4 mL of tetrahydrofuran, (2-(4-chloro-benzenesulfonylamino)-3-phenyl-propionamide (75 mg, 0.2 mmol), and methyl-4-hydroxybenzoate (73 mg, 0.4 mmol). The reaction is allowed to warm to room temperature (rt) and stirred overnight. The solvent is removed and the resultant residue purified by silica gel chromatography to provide the title compound. C13 NMR (100 MHz, CDCl3) 35.5, 48.7, 52.4, 61.4, 127.1, 128.8, 128.9, 129.0, 129.3, 129.6, 129.9, 136.8, 138.1, 139.8, 141.7, 166.9, 171.0. MS 487.1 m/z (M+1).

Preparation 3

(R)-2-(4-Chloro-benzenesulfonylamino)-2-phenyl-acetamide

To a solution of D-(−)-2-Amino-2-phenyl-acetamide (6.0 g, 40 mmol) in 150 mL of methylene chloride is added triethylamine (6.9 mL, 50 mmol) and 4-chlorobenzensulfonylchloride (8.43 g, 40 mmol) at 0° C. The reaction is warmed to room temperature and stirred overnight. The reaction is quenched with sodium bicarbonate and methylene chloride is added. The solid is filtered, washed with water and ether and dried in vacuo to provide 12.3 g of the title compound. C13 NMR (100 MHz, CD3OD) 60.3, 127.3, 128.1, 128.4, 128.7, 128.9, 137.1, 138.5, 139.7, 172.9. MS 325.1 m/z (M+1).

(R)-2-(4-chloro-benzenesulfonylamino)-2-(4-fluoro-phenyl)-acetamide

The title compound was synthesized according to the procedure of Preparation 3 employing (R)-2-amino-2-(4-fluoro-phenyl)-acetamide and 4-chlorobenzenesulfonylchloride to afford the desired product. 1HNMR (400 MHz, CD3OD)δ 4.87 (s, 1H), 6.94 (m, 2H), 7.24 m, 2H), 7.6 (dd, 4H, J=2.1, 103).

Example 2

(R)-4-{(Carbamoyl-phenyl-methyl)-(4-chloro-benzenesulfonyl)-amino]-methyl}-benzoic acid methyl ester To a solution of triphenylphosphine (48 mmg, 0.2 mmol) in 0.7 mL of tetrahydrofuran is added diisopropyl azodicarboxylate (0.04 mL, 0.2 mmol) and the reaction stirred for 30 min. To the reaction is added 0.4 mL of tetrahydrofuran, (R)-2-(4-chloro-benzenesulfonylamino)-2-phenyl-acetamide (32 mg, 0.2 mmol), and methyl-4-hydroxymethylbenzoate (73 mg, 0.2 mmol). The reaction is allowed to warm to room temperature and stirred overnight. The solvent is removed and the resultant residue purified by silica gel chromatography to provide the title compound. C13 NMR (100 MHz, CDCl3) 49.9, 52.3, 64.4, 127.9, 129.0, 129.2, 129.4, 129.5, 130.1, 133.5, 139.7, 142.5, 167.0, 171.0. MS 473.1 m/z (M+1).

Example 2A (R)-4-{[[Carbamoyl-(4-fluoro-phenyl)-methyl]-(4-chloro-benzenesulfonyl)-amino]-methyl}-benzoic acid methyl ester The title compound was prepared employing the procedure in Example 2 using (R)-2-(4-chloro-benzenesulfonylamino)-2-(4-fluoro-phenyl)-acetamide and methyl-4-hydroxymethylbenzoate to afford the desired product. Diagnostic 13CNMR (100 MHz, CDCl3) 49.9, 52.3, 63.4, 116.0, 116.2, 127.9, 129.1, 129.5, 129.6, 132.0, 132.1, 139.8, 142.3. MS 491.2 m/z (M+1).

Example 3

(R)-2-[(4-Chloro-benzenesulfonyl)-(4-dimethylaminomethyl-benzyl)-amino]-2-phenyl-acetamide The title compound was prepared employing the procedure detailed in Example 2, using (4-dimethylaminomethyl-phenyl)-methanol to afford the desired product (10 mg, 3% yield); 13CNMR (100 MHz, CDCl3) 45.3, 50.1, 64.0, 64.8, 128.5, 129.0, 129.1, 129.2, 129.3, 129.6, 130.2, 133.9, 135.7, 138.7, 139.4, 171.5 MS 472.1 m/z (M+1).

Example 4

(R)-2-[(4-Chloro-benzenesulfonyl)-(4-morpholin-4-ylmethyl-benzyl)-amino]-2-phenyl-acetamide The title compound was prepared employing the procedure detailed in Example 2, using (4-morpholin-4-ylmethyl-phenyl)-methanol to afford the desired product (170 mg, 43% yield); 13CMNR (100 MHz, CDCl3) 50.1, 53.7, 63.2, 64.8, 67.2, 128.5, 129.0, 129.1, 129.2, 129.3, 130.2, 133.9, 135.7, 138.7, 139.4, 171.4 MS 514.1 m/z (M+1).

Example 5

(R)-2-[Benzyl-(4-chloro-benzenesulfonyl)-amino]-2-phenyl-acetamide

To a solution of (R)-2-(4-chloro-benzenesulfonylamino)-2-phenyl-acetamide (350 mg, 1.1 mmol) in 4 mL of dimethylformamide are added benzylbromide (0.18 mL, 1.1 mmol) and potassium carbonate (179 mg, 1.3 mmol). The reaction is heated overnight at 50° C., poured into water/methylene chloride and extracted with methylene chloride. The combined organics are dried with sodium sulfate, concentrated in vacuo, and the resultant residue purified on silica gel chromatography to provide the title compound. C13 NMR (100 MHz, CDCl3) 50.3, 64.8, 127.6, 128.4, 128.6, 129.0, 129.1, 129.3, 129.4, 130.2, 133.9, 136.8, 138.6, 139.4, 171.7. MS 415.1 m/z (M+1).

Example 6

(R)-2-[(4-Chloro-benzenesulfonyl)-(4-cyano-benzyl)-amino]-2-phenyl-acetamide

The title compound was prepared in a manner analogous to that in Example 5, utilizing 4-cyanobenzyl bromide to provide the desired product in 50% yield; 13C NMR (100 MHz, CDCl3) 49.6, 63.8, 110.7, 119.0, 128.4, 129.1, 129.2, 129.5, 129.6, 130.0, 131.8, 133.5, 138.0, 139.8, 143.2, 170.8. MS 440.4 m/z (M+1).

Example 7

(R)-2-[(4-tert-Butyl-benzyl)-(4-chloro-benzenesulfonyl)-amino]-2-phenyl-acetamide The title compound was prepared as detailed in Example 5, utilizing 1-bromomethyl-4-tert-butyl-benzene to afford the desired product in 28% yield; 13CNMR (100 MHz, CDCl3) 31.5, 34.6, 50.1, 65.0, 125.3, 128.6, 129.0, 129.1, 129.2, 130.2, 133.3, 134.1, 139.2, 150.8, 171.6. MS 471.1 m/z (M+1).

Example 8

(R)-2-[(4-Chloro-benzenesulfonyl)-(3-cyano-benzyl)-amino]-2-phenyl-acetamide

The title compound was prepared as detailed in Example 5, utilizing 3-bromomethyl-benzonitrile to afford the desired product in 49% yield; 13CNMR (100 MHz, CDCl3) 49.3, 63.7, 112.0, 118.9, 128.8, 129.1, 129.3, 129.5, 129.7, 130.0, 130.7, 131.6, 132.5, 133.6, 139.1, 139.8, 170.9. MS 440.0 m/z (M+1).

Example 9

(R)-2-[(4-Chloro-benzenesulfonyl)-(4-trifluoromethoxy-benzyl)-amino]-2-phenyl-acetamide The title compound was prepared as detailed in Example 5, utilizing 1-bromomethyl-4-trifluoromethoxy-benzene to afford the desired product in 49% yield; 13CNMR (100 MHz, CDCl3) 49.4, 64.2, 120.7, 129.0, 129.2, 129.3, 129.4, 129.8, 130.0, 133.7, 135.8, 138.5, 138.6, 148.3, 171.0. MS 499.0 m/z (M+1).

Example 10

(R)-2-[(4-Chloro-benzenesulfonyl)-(4-oxazol-2-yl-benzyl)-amino]-2-phenyl-acetamide The title compound was prepared as detailed in Example 5, utilizing 4-(4-bromomethyl-phenyl)-[1,2,3]thiadiazole to afford the product in 8% yield; 13CNMR (100 MHz, CDCl3) 50.0, 64.6, 127.3, 127.9, 128.7, 129.1, 129.2, 129.3, 129.4, 129.5, 129.9, 130.1, 133.8, 138.5, 139.6, 162.7, 171.2. MS 499.0 m/z (M+1).

Example 11

(R)-2-[(4-Chloro-benzenesulfonyl)-(4-oxazol-2-yl-benzyl)-amino]-2-phenyl-acetamide The title compound was prepared as detailed in Example 5 utilizing 2-(4-bromomethyl-phenyl)-oxazole to afford the title compound in 4% yield; 13CNMR (100 MHz, CDCl3) 50.0, 64.5, 126.3, 126.5, 128.6, 129.2, 129.4, 129.5, 130.1, 133.6, 138.7, 139.5, 139.6, 171.1. MS 482.0 m/z (M+1).

Example 12

(R)-2-{(4-Chloro-benzenesulfonyl)-[4-(3-methyl-[1,2,4]oxadiazol-5-yl)-benzyl]-amino}-2-phenyl-acetamide The title compound was prepared in the manner outlined in Example 5, utilizing 5-(4-bromomethyl-phenyl)-3-methyl-[1,2,4]oxadiazole to afford the product in 14% yield; 13C NMR (100 MHz, CDCl3) 11.9, 49.8, 64.1, 122.9, 127.8, 128.6, 129.1, 129.2, 129.4, 129.5, 130.1, 133.5, 138.2, 139.7, 142.6, 168.0, 170.9, 175.4 MS 497.1 m/z (M+1).

Example 13

(R)-2-{(4-Chloro-benzenesulfonyl)-[4-(2-methyl-2H-tetrazol-5-yl)-benzyl]-amino}-2-phenyl-acetamide The title compound was prepared in the manner outlined in Example 5, utilizing 5-(4-bromomethyl-phenyl)-2-methyl-2H-tetrazole to afford the product in 5% yield; Diagnostic 13CNMR (100 MHz, CDCl3) 39.7, 50.0, 64.6, 126.4, 126.7, 127.2, 128.8, 129.2, 129.4, 130.1, 139.4, 139.6, 165.1, 171.1.

Example 14

(R)-2-{(4-Chloro-benzenesulfonyl)-[4-(1-hydroxy-1-methyl-ethyl)-benzyl]-amino}-2-phenyl-acetamide (R)-4-{[(1—Carbamoyl-phenyl-methyl)-(4-chloro-benzenesulfonyl)-amino]-methyl}-benzoic acid methyl ester (300 mg, 0.63 mmol) was dissolved in 1 mL THF and the solution was chiled in an ice bath. 3.0 M MeMgBr in diethyl ether (0.63 ml, 1.9 mmol) was added and the reaction mixture was stirred for 45 min. An additional portion of MeMgBr (0.63 ml, 1.9 mmol) was added and, after 30 min, the reaction was quenched by slow addition of water. The quenched reaction mixture was diluted with aqueous sodium bicarbonate and extracted with dichloromethane. After drying (sodium sulfate) the combined organics were concentrated to an oil. Purification on a silica gel flash column (40% EtOAc in hexanes) afforded 31 mg (10% yield) of the title compound.

Preparation 4

(R)-2-(2,2-Dimethyl-propylamino)-2-phenyl-acetamide

D-(−)-2-Amino-2-phenyl-acetamide (1.0 g, 6.7 mmol) was partially dissolved in 20 ml dichloromethane and treated with trimethylacetaldehyde (723 uL, 6.7 mmol). After stirring 20 min at room temperature, sodium triacetoxyborohydride (1.77 g, 8.4 mmol) was added and the resulting mixture was stirred at room temperature (rt) for 18 h. After diluting with aqueous sodium bicarbonate, the mixture was extracted with dichloromethane. The combined organics were dried ($Na_2SO_4$) and concentrated to a white solid (1.43 g, 97% yield). MS 221.2 m/z (M+1).

Example 15

(R)-2-[(4-Chloro-benzenesulfonyl-(2,2-dimethyl-propyl)-amino]-2-phenyl-acetamide (R)-2-(2,2-Dimethyl-propylamino)-2-phenyl-acetamide (700 mg, 3.2 mmol) was dissolved in dichloromethane (15 mL) and chilled in an ice bath. The solution was treated with triethylamine (553 uL, 4.0 mmol) followed by 4-chlorobenzenesulfonyl chloride (671 mg, 3.2 mmol). After heating at 50° C. for 18 h, the mixture was cooled, diluted with aqueous sodium bicarbonate and extracted with dichloromethane. The combined organic extracts were dried ($Na_2SO_4$) and concentrated to an oil. Purification on a silica gel flash column (40% EtOAc in hexanes, eluent) afforded the title compound in 3% yield. 13CNMR (100 MHz, CDCl3) 28.6, 33.2, 62.7, 70.0, 128.8, 129.0, 121.1, 129.2, 130.7, 133.6, 138.7, 139.0, 172.7. MS 395.1 m/z (M+1).

Examples 16–77

(R)-2-(4-Chloro-benzenesulfonylamino)-2-phenyl-acetamide (24.3 mg, 0.075 mmol) was dissolved in 0.41 ml DMF. The resulting solution was cooled to 0° C. and 1 N potassium t-butoxide in THF (0.09 ml, 0.09mmol) was added. After warming to room temperature, the solution was added to a benzyl bromide (0.075 mmol) that is substituted as indicated in the respective definitions of $R^3$ in the Examples recited in Table 1 below, and the reaction mixture was heated at 60° C. overnight. After cooling and diluting with water, the organics were extracted with dichloromethane, dried with sodium sulfate and concentrated. The samples were purified on a Waters Xterra PrepMS $C_{18}$ column (5 uM, 30×100 mm) eluting with 0.1% TFA in water and acetonitrile in a gradient system.

Examples 16–77 in Table 1 were synthesized by methods analogous to those described above.

TABLE 1

| Ex | Theo. Mass | Obs. MS m/z (M + 1) | HPLC RT (min) | Name |
|---|---|---|---|---|
| 16 | 428.1 | 429.0 | 2.38 | (R)-2-[(4-Chloro-benzenesulfonyl)-(2-methyl-benzyl)-amino]-2-phenyl-acetamide |
| 17 | 428.1 | 429.0 | 2.46 | (R)-2-[(4-Chloro-benzenesulfonyl)-(3-methyl-benzyl)-amino]-2-phenyl-acetamide |
| 18 | 448.0 | 449.0 | 2.49 | (R)-2-[(4-Chloro-benzenesulfonyl)-(3-chloro-benzyl)-amino]-2-phenyl-acetamide |
| 19 | 439.1 | 440.0 | 2.31 | (R)-2-[(4-Chloro-benzenesulfonyl)-(2-cyano-benzyl)-amino]-2-phenyl-acetamide |
| 20 | 432.0 | 433.0 | 2.39 | (R)-2-[(4-Chloro-benzenesulfonyl)-(3-fluoro-benzyl)-amino]-2-phenyl-acetamide |
| 21 | 432.0 | 433.0 | 2.39 | (R)-2-[(4-Chloro-benzenesulfonyl)-(4-fluoro-benzyl)-amino]-2-phenyl-acetamide |
| 22 | 482.0 | 483.0 | 2.56 | (R)-2-[(4-Chloro-benzenesulfonyl)-(4-trifluoromethyl-benzyl)-amino]-2-phenyl-acetamide |
| 23 | 450.0 | 451.0 | 2.43 | (R)-2-[(4-Chloro-benzenesulfonyl)-(2,4-difluoro-benzyl)-amino]-2-phenyl-acetamide |
| 24 | 450.0 | 451.0 | 2.44 | (R)-2-[(4-Chloro-benzenesulfonyl)-(3,4-difluoro-benzyl)-amino]-2-phenyl-acetamide |
| 25 | 482.1 | 483.0 | 2.52 | (R)-2-[(4-Chloro-benzenesulfonyl)-(3-trifluoromethyl-benzyl)-amino]-2-phenyl-acetamide |
| 26 | 482.1 | 483.1 | 2.5 | (R)-2-[(4-Chloro-benzenesulfonyl)-(2-trifluoromethyl-benzyl)-amino]-2-phenyl-acetamide |
| 27 | 448.0 | 449.0 | 2.45 | (R)-2-[(4-Chloro-benzenesulfonyl)-(2-chloro-benzyl)-amino]-2-phenyl-acetamide |
| 28 | 484.0 | 485.0 | 2.48 | (R)-2-[(4-Chloro-benzenesulfonyl)-(2,6-dichloro-benzyl)-amino]-2-phenyl-acetamide |
| 29 | 432.1 | 433.1 | 2.37 | (R)-2-[(4-Chloro-benzenesulfonyl)-(2-fluoro-benzyl)-amino]-2-phenyl-acetamide |
| 30 | 450.1 | 451.1 | 2.36 | (R)-2-[(4-Chloro-benzenesulfonyl)-(2,6-difluoro-benzyl)-amino]-2-phenyl-acetamide |
| 31 | 516.0 | 517.0 | 2.61 | (R)-2-[(4-Chloro-benzenesulfonyl)-(2-chloro-5-trifluoromethyl-benzyl)-amino]-2-phenyl-acetamide |
| 32 | 480.1 | 481.1 | 2.42 | (R)-2-[(4-Chloro-benzenesulfonyl)-(3-difluoromethoxy-benzyl)-amino]-2-phenyl-acetamide |
| 33 | 500.1 | 501.1 | 2.58 | (R)-2-[(4-Chloro-benzenesulfonyl)-(3-fluoro-4-trifluoromethyl-benzyl)-amino]-2-phenyl-acetamide |
| 34 | 500.1 | 501.1 | 2.54 | (R)-2-[(4-Chloro-benzenesulfonyl)-(5-fluoro-2-trifluoromethyl-benzyl)-amino]-2-phenyl-acetamide |
| 35 | 498.1 | 499.1 | 2.55 | (R)-2-[(4-Chloro-benzenesulfonyl)-(2-trifluoromethoxy-benzyl)-amino]-2-phenyl-acetamide |
| 36 | 502.1 | 503.1 | 2.35 | (R)-4-{[(Carbamoyl-phenyl-methyl)-(4-chloro-benzenesulfonyl)-amino]-methyl}-3-methoxy-benzoic acid methyl ester |
| 37 | 490.1 | 491.1 | 2.61 | (R)-2-[Biphenyl-2-ylmethyl-(4-chloro-benzenesulfonyl)-amino]-2-phenyl-acetamide |
| 38 | 568.1 | 569.1 | 2.38 | (R)-2-[(2-Benzenesulfonylmethyl-benzyl)-(4-chloro-benzenesulfonyl)-amino]-2-phenyl-acetamide |
| 39 | 450.1 | 451.1 | 2.42 | (R)-2-[(4-Chloro-benzenesulfonyl)-(2,3-difluoro-benzyl)-amino]-2-phenyl-acetamide |
| 40 | 450.1 | 451.1 | 2.44 | (R)-2-[(4-Chloro-benzenesulfonyl)-(3,5-difluoro-benzyl)-amino]-2-phenyl-acetamide |
| 41 | 468.0 | 469.0 | 2.37 | (R)-2-[(4-Chloro-benzenesulfonyl)-(2,3,6-trifluoro-benzyl)-amino]-2-phenyl-acetamide |

TABLE 1-continued

| Ex | Theo. Mass | Obs. MS m/z (M + 1) | HPLC RT (min) | Name |
|---|---|---|---|---|
| 42 | 472.1 | 473.1 | 2.31 | (R)-3-{[(Carbamoyl-phenyl-methyl)-(4-chloro-benzenesulfonyl)-amino]-methyl}-benzoic acid methyl ester |
| 43 | 484.0 | 485.0 | 2.61 | (R)-2-[(4-Chloro-benzenesulfonyl)-(3,4-dichloro-benzyl)-amino]-2-phenyl-acetamide |
| 44 | 446.1 | 447.1 | 2.48 | (R)-2-[(4-Chloro-benzenesulfonyl)-(2-fluoro-3-methyl-benzyl)-amino]-2-phenyl-acetamide |
| 45 | 468.1 | 469.1 | 2.46 | (R)-2-[(4-Chloro-benzenesulfonyl)-(2,4,5-trifluoro-benzyl)-amino]-2-phenyl-acetamide |
| 46 | 468.1 | 469.0 | 2.41 | (R)-2-[(4-Chloro-benzenesulfonyl)-(2,4,6-trifluoro-benzyl)-amino]-2-phenyl-acetamide |
| 47 | 466.0 | 467.0 | 2.52 | (R)-2-[(4-Chloro-benzenesulfonyl)-(2-chloro-4-fluoro-benzyl)-amino]-2-phenyl-acetamide |
| 48 | 524.1 | 525.1 | 2.65 | (R)-2-{(4-Chloro-benzenesulfonyl)-[3-(4-fluoro-phenoxyl)-benzyl]-amino}-2-phenyl-acetamide |
| 49 | 515.1 | 516.1 | 2.52 | (R)-2-[(4-Chloro-benzenesulfonyl)-(2'-cyano-biphenyl-4-ylmethyl)-amino]-2-phenyl-acetamide |
| 50 | 428.1 | 429.1 | 2.46 | (R)-2-[(4-Chloro-benzenesulfonyl)-(4-methyl-benzyl)-amino]-2-phenyl-acetamide |
| 51 | 459.1 | 460.1 | 2.35 | (R)-2-[(4-Chloro-benzenesulfonyl)-(3-nitro-benzyl)-amino]-2-phenyl-acetamide |
| 52 | 489.1 | 490.1 | 2.33 | (R)-2-[(4-Chloro-benzenesulfonyl)-(2-methoxy-5-nitro-benzyl)-amino]-2-phenyl-acetamide |
| 53 | 475.1 | 476.1 | 2.21 | (R)-2-[(4-Chloro-benzenesulfonyl)-(2-hydroxy-5-nitro-benzyl)-amino]-2-phenyl-acetamide |
| 54 | 459.1 | 460.1 | 2.38 | (R)-2-[(4-Chloro-benzenesulfonyl)-(4-nitro-benzyl)-amino]-2-phenyl-acetamide |
| 55 | 450.1 | 451.1 | 2.40 | (R)-2-[(4-Chloro-benzenesulfonyl)-(2,5-difluoro-benzyl)-amino]-2-phenyl-acetamide |
| 56 | 512.0 | 513.0 | 2.58 | (R)-2-[(4-Bromo-2-fluoro-benzyl)-(4-chloro-benzenesulfonyl)-amino]-2-phenyl-acetamide |
| 57 | 500.1 | 501.1 | 2.55 | (R)-2-[(4-Chloro-benzenesulfonyl)-(4-fluoro-2-trifluoromethyl-benzyl)-amino]-2-phenyl-acetamide |
| 58 | 498.1 | 499.1 | 2.58 | (R)-2-[(4-Chloro-benzenesulfonyl)-(3-trifluoromethoxy-benzyl)-amino]-2-phenyl-acetamide |
| 59 | 519.1 | 520.1 | 2.29 | (R)-2-[(4-Chloro-benzenesulfonyl)-(4,5-dimethoxy-2-nitro-benzyl)-amino]-2-phenyl-acetamide |
| 60 | 444.1 | 445.1 | 2.33 | (R)-2-[(4-Chloro-benzenesulfonyl)-(3-methoxy-benzyl)-amino]-2-phenyl-acetamide |
| 61 | 475.1 | 475.1 | 2.33 | (R)-2-[(4-Chloro-benzenesulfonyl)-(3,5-dimethoxy-benzyl)-amino]-2-phenyl-acetamide |
| 62 | 514.0 | 515.1 | 2.71 | (R)-2-[(4-Chloro-benzenesulfonyl)-(4-trifluoromethylsulfanyl-benzyl)-amino]-2-phenyl-acetamide |
| 63 | 518.1 | 519.1 | 2.50 | (R)-2-[(4-Benzoyl-benzyl)-(4-chloro-benzenesulfonyl)-amino]-2-phenyl-acetamide |
| 64 | 605.1 | 606.1 | 2.77 | (R)-2-[(4-Butoxy-2-trifluoromethyl-quinolin-6-ylmethyl)-(4-chloro-benzenesulfonyl)-amino]-2-phenyl-acetamide |
| 65 | 524.2 | 525.2 | 3.02 | (R)-2-[(4-Chloro-benzenesulfonyl)-(5,5,8,8-tetramethyl-5,6,7,8-tetrahydro-naphthalen-2-ylmethyl)-amino]-2-phenyl-acetamide |
| 66 | 520.1 | 521.1 | 2.65 | (R)-2-[(3-Benzyloxy-benzyl)-(4-chloro-benzenesulfonyl)-amino]-2-phenyl-acetamide |
| 67 | 480.1 | 481.1 | 2.29 | (R)-2-[(4-Chloro-benzenesulfonyl)-(4-pyrazol-1-yl-benzyl)-amino]-2-phenyl-acetamide |
| 68 | 442.1 | 443.1 | 2.58 | (R)-2-[(4-Chloro-benzenesulfonyl)-(4-ethyl-benzyl)-amino]-2-phenyl-acetamide |
| 69 | 513.2 | 514.2 | 2.27 | (R)-N-Butyl-4-{[(carbamoyl-phenyl-methyl)-(4-chloro-benzenesulfonyl)-amino]-methyl}-benzamide |
| 70 | 471.1 | 472.1 | 1.92 | (R)-4-{[(Carbamoyl-phenyl-methyl)-(4-chloro-benzenesulfonyl)-amino]-methyl}-N-methyl-benzamide |
| 71 | 590.1 | 591.1 | 2.44 | (R)-(4-{[(Carbamoyl-phenyl-methyl)-(4-chloro-benzenesulfonyl)-amino]-methyl}-phenyl)-acetic acid 2-oxo-2-phenyl-ethyl ester |
| 72 | 550.1 | 551.1 | 2.70 | (R)-2-[(3,5-Bis-trifluoromethyl-benzyl)-(4-chloro-benzenesulfonyl)-amino]-2-phenyl-acetamide |
| 73 | 518.1 | 519.1 | 2.52 | (R)-2-[(4-Benzoyl-benzyl)-(4-chloro-benzenesulfonyl)-amino]-2-phenyl-acetamide |
| 74 | 524.1 | 525.1 | 2.59 | (R)-2-{(4-Chloro-benzenesulfonyl)-[3-(2-fluoro-phenoxy)-benzyl]-amino}-2-phenyl-acetamide |
| 75 | 448.0 | 449.1 | 2.52 | (R)-2-[(4-Chloro-benzenesulfonyl)-(4-chloro-benzyl)-amino]-2-phenyl-acetamide |
| 76 | 442.1 | 443.1 | 2.56 | (R)-2-[(4-Chloro-benzenesulfonyl)-(3,5-dimethyl-benzyl)-amino]-2-phenyl-acetamide |
| 77 | 500.1 | 501.1 | 2.56 | (R)-2-[(4-Chloro-benzenesulfonyl)-(4-fluoro-3-trifluoromethyl-benzyl)-amino]-2-phenyl-acetamide |

Examples 78–105

To the appropriate sulfonyl chloride (0.15 mmol) was added a slurry of 4-{[(carbamoyl-phenyl-methyl)-amino]-methyl}-benzoic acid methyl ester (0.1 mmol) in hot dichloroethane containing diisopropylethylamine (0.2 mmol). The resulting mixture was heated at 80° C. for 48 hours. The cooled reaction mixture was poured into 1.5 ml 1M NaOH and extracted three times with dichloromethane. The combined extracts were dried ($Na_2SO_4$) and concentrated. The samples were purified on a Waters Xterra PrepMS $C_{18}$ column (5 uM, 19×100 mm) eluting with 0.1% TFA in water and acetonitrile in a gradient system.

Examples 78–105 in Table 2 were synthesized by methods analogous to those described above.

TABLE 2

| Ex. | Theo. Mass | Obs. MS m/z (M + 1) | HPLC RT (min) | Name |
|---|---|---|---|---|
| 78 | 522.11 | 523.11 | 2.61 | (R)-4-{[(Carbamoyl-phenyl-methyl)-(4-trifluoromethoxy-benzenesulfonyl)-amino]-methyl}-benzoic acid methyl ester |
| 79 | 463.12 | 464.12 | 2.33 | (R)-4-{[(Carbamoyl-phenyl-methyl)-(4-cyano-benzenesulfonyl)-amino]-methyl}-benzoic acid methyl ester |
| 80 | 486.1 | 487.1 | 2.57 | (R)-4-{[(Carbamoyl-phenyl-methyl)-(3-chloro-4-methyl-benzenesulfonyl)-amino]-methyl}-benzoic acid methyl ester |
| 81 | 456.1 | 457.1 | 2.38 | (R)-4-{[(Carbamoyl-phenyl-methyl)-(3-fluoro-benzenesulfonyl)-amino]-methyl}-benzoic acid methyl ester |
| 82 | 492.1 | 493.1 | 2.48 | (R)-4-{[(Carbamoyl-phenyl-methyl)-(2,3,4-trifluoro-benzenesulfonyl)-amino]-methyl}-benzoic acid methyl ester |
| 83 | 474.1 | 475.1 | 2.42 | (R)-4-{[(Carbamoyl-phenyl-methyl)-(3,4-difluoro-benzenesulfonyl)-amino]-methyl}-benzoic acid methyl ester |
| 84 | 518.0 | 519.0 | 2.50 | (R)-4-{[(3-Bromo-benzenesulfonyl)-(carbamoyl-phenyl-methyl)-amino]-methyl}-benzoic acid methyl ester |
| 85 | 452.1 | 453.1 | 2.42 | (R)-4-{[(Carbamoyl-phenyl-methyl)-(toluene-4-sulfonyl)-amino]-methyl}-benzoic acid methyl ester |
| 86 | 438.1 | 439.1 | 2.29 | (R)-4-{[Benzenesulfonyl-(carbamoyl-phenyl-methyl)-amino]-methyl}-benzoic acid methyl ester |
| 87 | 518.0 | 519.1 | 2.54 | (R)-4-{[(4-Bromo-benzenesulfonyl)-(carbamoyl-phenyl-methyl)-amino]-methyl}-benzoic acid methyl ester |
| 88 | 506.1 | 507.1 | 2.54 | (R)-4-{[(Carbamoyl-phenyl-methyl)-(3-trifluoromethyl-benzenesulfonyl)-amino]-methyl}-benzoic acid methyl ester |
| 89 | 456.1 | 457.1 | 2.36 | (R)-4-{[(Carbamoyl-phenyl-methyl)-(4-fluoro-benzenesulfonyl)-amino]-methyl}-benzoic acid methyl ester |
| 90 | 468.1 | 469.1 | 2.33 | (R)-4-{[(Carbamoyl-phenyl-methyl)-(4-methoxy-benzenesulfonyl)-amino]-methyl}-benzoic acid methyl ester |
| 91 | 452.1 | 453.1 | 2.40 | (R)-4-{[(Carbamoyl-phenyl-methyl)-(toluene-3-sulfonyl)-amino]-methyl}-benzoic acid methyl ester |
| 92 | 472.1 | 473.1 | 2.38 | (R)-4-{[(Carbamoyl-phenyl-methyl)-(2-chloro-benzenesulfonyl)-amino]-methyl}-benzoic acid methyl ester |
| 93 | 490.1 | 491.1 | 2.52 | (R)-4-{[(Carbamoyl-phenyl-methyl)-(3-chloro-4-fluoro-benzenesulfonyl)-amino]-methyl}-benzoic acid methyl ester |
| 94 | 474.1 | 475.1 | 2.38 | (R)-4-{[(Carbamoyl-phenyl-methyl)-(2,4-difluoro-benzenesulfonyl)-amino]-methyl}-benzoic acid methyl ester |
| 95 | 474.1 | 475.1 | 2.44 | (R)-4-{[(Carbamoyl-phenyl-methyl)-(3,5-difluoro-benzenesulfonyl)-amino]-methyl}-benzoic acid methyl ester |
| 96 | 517.1 | 518.1 | 2.52 | (R)-4-{[(Carbamoyl-phenyl-methyl)-(4-chloro-3-nitro-benzenesulfonyl)-amino]-methyl}-benzoic acid methyl ester |
| 97 | 470.1 | 471.1 | 2.48 | (R)-4-{[(Carbamoyl-phenyl-methyl)-(5-fluoro-2-methyl-benzenesulfonyl)-amino]-methyl}-benzoic acid methyl ester |
| 98 | 506.1 | 507.1 | 2.54 | (R)-4-{[(Carbamoyl-phenyl-methyl)-(2,3-dichloro-benzenesulfonyl)-amino]-methyl}-benzoic acid methyl ester |
| 99 | 532.1 | 533.1 | 2.61 | (R)-4-{[(4-Bromo-2-methyl-benzenesulfonyl)-(carbamoyl-phenyl-methyl)-amino]-methyl}-benzoic acid methyl ester |
| 100 | 522.1 | 523.1 | 2.52 | (R)-4-{[(Carbamoyl-phenyl-methyl)-(2-trifluoromethoxy-benzenesulfonyl)-amino]-methyl}-benzoic acid methyl ester |
| 101 | 498.1 | 499.1 | 2.23 | (R)-4-{[(Carbamoyl-phenyl-methyl)-(3,4-dimethoxy-benzenesulfonyl)-amino]-methyl}-benzoic acid methyl ester |
| 102 | 468.1 | 469.1 | 2.33 | (R)-4-{[(Carbamoyl-phenyl-methyl)-(4-chloro-2,5-dimethyl-benzenesulfonyl)-amino]-methyl}-benzoic acid methyl ester |

TABLE 2-continued

| Ex. | Theo. Mass | Obs. MS m/z (M + 1) | HPLC RT (min) | Name |
|---|---|---|---|---|
| 103 | 480.2 | 481.2 | 2.65 | (R)-4-{[(Carbamoyl-phenyl-methyl)-(4-isopropyl-benzenesulfonyl)-amino]-methyl}-benzoic acid methyl ester |
| 104 | 480.2 | 481.2 | 2.57 | (R)-4-{[(Carbamoyl-phenyl-methyl)-(4-propyl-benzenesulfonyl)-amino]-methyl}-benzoic acid methyl ester |
| 105 | 483.1 | 484.1 | 2.36 | (R)-4-{[(Carbamoyl-phenyl-methyl)-(3-nitro-benzenesulfonyl)-amino]-methyl}-benzoic acid methyl ester |

The invention described and claimed herein is not to be limited in scope by the embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A compound of the Formula I

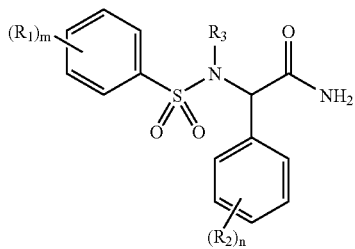

wherein $R^1$ and $R^2$ are each independently selected from —H, —$C_1$–$C_8$ alkyl, —$C_2$–$C_8$ alkenyl, —$C_1$–$C_8$ alkoxy, —$C_2$–$C_8$ alkenoxy, —$C_1$–$C_8$ hydroxyalkyl, —$C_2$–$C_8$ hydroxyalkenyl, -halo, —CN, —$NO_2$, —$(CH_2)_q NC(=O)R^6$, —$(CH_2)_q C(=O)OR^5$, —$(CH_2)_q C(=O)NR^6R^7$, —$(CH_2)q NR^6R^7$, $C_3$–$C_8$ cycloalkyl and —$C_5$–$C_8$ cycloalkenyl, wherein $R^1$ and $R^2$ are each optionally independently substituted with from one to three substituents independently selected from —$C_1$–$C_6$ alkoxy, —$C_1$–$C_6$ alkyl -halo and —OH;

$R^3$ is a group of the Formula II or the Formula III, each as depicted below

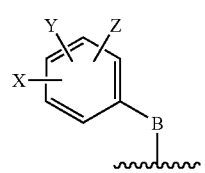

-continued

III

X—D
 |
 Y
  \
   Z
 /
B wherein B is absent or is selected from $C_1$–$C_8$ alkylene and $C_2$–$C_4$ alkenylene;

D is selected from —$C_1$–$C_8$ alkyl, —$C_3$–$C_{10}$ cycloalkyl, -(3–10 membered) heterocycloalkyl and -(5–7 membered) heteroaryl;

X, Y and Z are each independently selected from —H, —$C_1$–$C_8$ alkyl, —$C_2$–$C_8$ alkenyl, —$C_1$–$C_8$ alkoxy, —$C_2$–$C_8$ alkenoxy, —$C_1$–$C_8$ hydroxyalkyl, —$C_2$–$C_8$ hydroxyalkenyl, -halo, —OH, —CN, —$NO_2$, —$(CH_2)_q$—$NR^7R^8$, —$(CH_2)_q$—$NHC(=O)R^5$, —$(CH_2)_q$—$C(=O)R^9$, —$(CH_2)_q$—$C(=O)NR^7R^8$, —$(CH_2)_q$—$C(=O)OR^9$, —$(CH_2)_q$—$SO_2R^9$, —$S(C_1$–$C_8$ alkyl), —$C_3$–$C_8$ cycloalkyl, —$(CH_2)_q$—((3–10 membered) heterocycloalkyl), —$(CH_2)_q$—($C_6$–$C_{14}$ aryl), —$(CH_2)_q$—((4–10 membered) heteroaryl) and —$(CH_2)_q$—($C_6$–$C_{14}$ aryloxy);

wherein said X, Y and Z are each optionally independently substituted with from one to three substituents independently selected from —$C_1$–$C_8$ alkyl, —$C_2$–$C_8$ alkenyl, —$C_1$–$C_8$ alkoxy, —$C_2$–$C_8$ alkenoxy, $C_1$–$C_8$ hydroxyalkyl, —$C_2$–$C_8$ hydroxyalkenyl, halo, —OH and —CN;

and wherein said alkoxy substituent of X, Y and Z is optionally independently substituted with from one to three substituents independently selected from halo;

$R^5$, $R^6$, $R^7$, $R^8$ and $R^9$ are each independently selected from —H, —$C_1$–$C_{12}$ alkyl, —$C_2$–$C_{12}$ alkenyl, —$C_3$–$C_{10}$ cycloalkyl, —$C_5$–$C_{10}$ cycloalkenyl, —$C_5$–$C_{13}$ bicycloalkyl, —$C_7$–$C_{13}$ bicycloalkenyl, -(3–10 membered) heterocycloalkyl, —$C_6$–$C_{14}$ aryl and -(5–8 membered) heteroaryl;

wherein $NR^6R^7$ or $NR^7R^8$ may in each instance independently optionally form a -(3–8 membered) heterocycloalkyl;

m is 0, 1, 2 or 3;

n is 0, 1, 2 or 3; and q is 0, 1 or 2;

or a pharmaceutically acceptable salt thereof.

2. A compound according to claim 1, wherein $R^1$ is halo, $C_1$–$C_4$ alkyl, or $C_1$–$C_4$ alkoxy, and wherein said alkyl and alkoxy are optionally substituted with 1 to 3 halo atoms.

3. A compound according to claim 1, wherein $R^2$ is —H.

4. A compound according to claim 1, wherein $R^3$ is a group of the Formula III, as depicted below

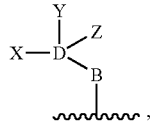
III wherein D is a —$C_1$–$C_8$ alkyl, and X, Y, Z and B are as defined in claim 1 above, and wherein said X, Y and Z are each optionally independently substituted according to claim 1 above.

5. A compound according to claim 1, wherein $R^3$ is a group of the Formula II, as depicted below

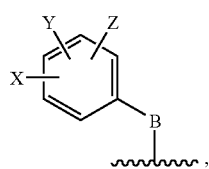
II wherein X, Y, Z and B are as defined in claim 1 above, and wherein X, Y and Z are each optionally independently substituted according to claim 1 above.

6. A compound according to claim 5, wherein $R^3$ is a group of the Formula II, as depicted below

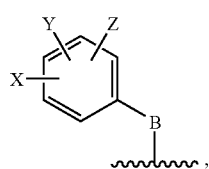
II wherein B is $C_1$–$C_8$ alkylene;

X, Y and Z are each independently selected from —H, —$C_1$–$C_8$ alkyl, —$C_2$–$C_8$ alkenyl, —$C_1$–$C_8$ alkoxy, —$C_2$–$C_8$ alkenoxy, -halo, —OH, —CN, —$NO_2$, —$(CH_2)_q$—$NR^7R^8$, —$(CH_2)_q$—$C(=O)NR^7R^8$, —$(CH_2)_q$—$C(=O)R^9$, —$(CH_2)_q$—$C(=O)OR^9$, —$S(C_1$–$C_8$ alkyl), —$(CH_2)_q$—$SO_2R^9$, —$(CH_2)_q$—((3–10 membered) heterocycloalkyl), —$(CH_2)_q$—($C_6$–$C_{14}$ aryl), —$(CH_2)_q$—((4–10 membered) heteroaryl) and —$(CH_2)_q$—($C_6$–$C_{14}$ aryloxy);

wherein said X, Y and Z are each optionally independently substituted with from one to three substituents independently selected from halo, —OH and —CN; and q is 0, 1 or 2.

7. A compound according to claim 6, wherein $R^3$ is a group of the Formula II, as depicted below

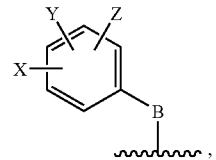
II wherein B is methylene; q is 1; and X, Y and Z are as defined in claim 6 above, wherein said X, Y and Z are each optionally independently substituted according to claim 6 above.

8. A compound according to claim 6, wherein $R^3$ is a group of the Formula II, as depicted below

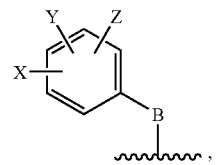
II wherein B is $C_1$–$C_8$ alkylene;

X, Y and Z are each independently selected from —H, —$C_1$–$C_8$ alkyl, —$C_2$–$C_8$ alkenyl, —$C_1$–$C_8$ alkoxy, —$C_2$–$C_8$ alkenoxy, -halo, —OH, —CN, —$NO_2$, —$(CH_2)_q$—$NR^7R^8$, —$(CH_2)_q$—$C(=O)NR^7R^8$, —$(CH_2)_q$—$C(=O)R^9$, —$(CH_2)_q$—$C(=O)OR^9$, —$S(C_1$–$C_8$ alkyl), —$(CH_2)_q$—$SO_2R^9$, —$(CH_2)_q$—((3–10 membered) heterocycloalkyl), —$(CH_2)_q$—($C_6$–$C_{14}$ aryl), —$(CH_2)_q$—((4–10 membered) heteroaryl) and —$(CH_2)_q$—($C_6$–$C_{14}$ aryloxy);

wherein said alkyl, alkenyl, alkoxy, alkenoxy, —$S(C_1$–$C_8$ alkyl), aryl and aryloxy of X, Y and Z are each optionally independently substituted with from one to three substituents independently selected from halo, —OH and —CN; and q is 0, 1 or 2.

9. A compound according to claim 8, wherein $R^3$ is a group of the Formula II, as depicted below

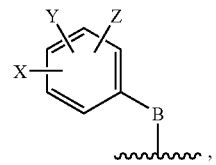
II wherein B is $C_1$–$C_8$ alkylene; q is 0, 1 or 2; and the aryl of said —$(CH_2)_q$—($C_6$–$C_{14}$ aryl) of X, Y and Z is phenyl, the $R^9$ of said —$(CH_2)_q$—$C(=O)R^9$ and of said —$(CH_2)_q$—$SO_2R^9$, both of X, Y and Z, is phenyl, and the aryloxy of said —$(CH_2)_q$—($C_6$–$C_{14}$ aryloxy) of X, Y and Z is phenoxy, wherein said X, Y and Z are each optionally independently substituted according to claim 8 above.

10. A compound according to claim 8, wherein $R^3$ is a group of the Formula II, as depicted below

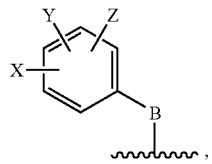

wherein B is $C_1$–$C_8$ alkylene; q is 0, 1 or 2; and the heterocycloalkyl of said —$(CH_2)_q$—(3–10 membered) heterocycloalkyl of X, Y and Z is selected from pyrrolidinyl and morpholinyl, wherein said X, Y and Z are each optionally independently substituted according to claim 8 above.

11. A compound according to claim 8, wherein $R^3$ is a group of the Formula II, as depicted below

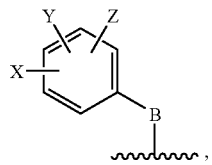

wherein B is $C_1$–$C_8$ alkylene; q is 0, 1 or 2; and the heteroaryl of said —$(CH_2)_q$—(4–10 membered) heteroaryl of X, Y and Z is selected from imidazolyl, thiadiazolyl, oxazolyl, pyrazolyl, isoxazolyl and tetrazolyl, wherein said X, Y and Z are each optionally independently substituted according to claim 8 above.

12. A compound according to claim 1, wherein $R^3$ is aryl or benzyl.

13. A compound according to claim 2, wherein said halo is chlorine and m is 1.

14. A compound according to claim 1 selected from the group consisting of:

4-{[(Carbamoyl-phenyl-methyl)-(4-chloro-benzenesulfonyl)-amino]-methyl}-benzoic acid methyl ester;
(R)-2-[(4-Chloro-benzenesulfonyl)-(4-dimethylaminomethyl-benzyl)-amino]-2-phenyl-acetamide;
(R)-2-[(4-Chloro-benzenesulfonyl)-(4-morpholin-4-ylmethyl-benzyl)-amino]-2-phenyl-acetamide;
(R)-2-[Benzyl-(4-chloro-benzenesulfonyl)-amino]-2-phenyl-acetamide;
(R)-2-[(4-Chloro-benzenesulfonyl)-(4-cyano-benzyl)-amino]-2-phenyl-acetamide;
(R)-2-[(4-tert-Butyl-benzyl)-(4-chloro-benzenesulfonyl)-amino]-2-phenyl-acetamide;
(R)-2-[(4-Chloro-benzenesulfonyl)-(3-cyano-benzyl)-amino]-2-phenyl-acetamide;
(R)-2-[(4-Chloro-benzenesulfonyl)-(4-trifluoromethoxy-benzyl)-amino]-2-phenyl-acetamide;
(R)-2-[(4-Chloro-benzenesulfonyl)-(4-[1,2,3]thiadiazol-4-yl-benzyl)-amino]-2-phenyl-acetamide;
(R)-2-[(4-Chloro-benzenesulfonyl)-(4-oxazol-2-yl-benzyl)-amino]-2-phenyl-acetamide;
(R)-2-{(4-Chloro-benzenesulfonyl)-[4-(3-methyl-[1,2,4]oxadiazol-5-yl)-benzyl]-amino}-2phenyl-acetamide;
(R)-2-{(4-Chloro-benzenesulfonyl)-[4-(2-methyl-2H-tetrazol-5-yl)-benzyl]-amino}-2-phenyl-acetamide;
(R)-2-{(4-Chloro-benzenesulfonyl)-[4-(1-hydroxy-1-methyl-ethyl)-benzyl]-amino}-2-phenyl-acetamide;
(R)-2-[(4-Chloro-benzenesulfonyl)-(2,2-dimethyl-propyl)-amino]-2-phenyl-acetamide;
(R)-2-[(4-Chloro-benzenesulfonyl)-(2-methyl-benzyl)-amino]-2-phenyl-acetamide;
(R)-2-[(4-Chloro-benzenesulfonyl)-(3-methyl-benzyl)-amino]-2-phenyl-acetamide;
(R)-2-[(4-Chloro-benzenesulfonyl)-(3-chloro-benzyl)-amino]-2-phenyl-acetamide;
(R)-2-[(4-Chloro-benzenesulfonyl)-(2-cyano-benzyl)-amino]-2-phenyl-acetamide;
(R)-2-[(4-Chloro-benzenesulfonyl)-(3-fluoro-benzyl)-amino]-2-phenyl-acetamide;
(R)-2-[(4-Chloro-benzenesulfonyl)-(4-fluoro-benzyl)-amino]-2-phenyl-acetamide;
(R)-2-[(4-Chloro-benzenesulfonyl)-(4-trifluoromethyl-benzyl)-amino]-2-phenyl-acetamide;
(R)-2-[(4-Chloro-benzenesulfonyl)-(2,4-difluoro-benzyl)-amino]-2-phenyl-acetamide;
(R)-2-[(4-Chloro-benzenesulfonyl)-(3,4-difluoro-benzyl)-amino]-2-phenyl-acetamide;
(R)-2-[(4-Chloro-benzenesulfonyl)-(3-trifluoromethyl-benzyl)-amino]-2-phenyl-acetamide;
(R)-2-[(4-Chloro-benzenesulfonyl)-(2-trifluoromethyl-benzyl)-amino]-2-phenyl-acetamide;
(R)-2-[(4-Chloro-benzenesulfonyl)-(2-chloro-benzyl)-amino]-2-phenyl-acetamide;
(R)-2-[(4-Chloro-benzenesulfonyl)-(2,6-dichloro-benzyl)-amino]-2-phenyl-acetamide;
(R)-2-[(4-Chloro-benzenesulfonyl)-(2-fluoro-benzyl)-amino]-2-phenyl-acetamide;
(R)-2-[(4-Chloro-benzenesulfonyl)-(2,6-difluoro-benzyl)-amino]-2-phenyl-acetamide;
(R)-2-[(4-Chloro-benzenesulfonyl)-(2-chloro-5-trifluoromethyl-benzyl)-amino]-2-phenyl-acetamide;
(R)-2-[(4-Chloro-benzenesulfonyl)-(3-difluoromethoxy-benzyl)-amino]-2-phenyl-acetamide;
(R)-2-[(4-Chloro-benzenesulfonyl)-(3-fluoro-4-trifluoromethyl-benzyl)-amino]-2-phenyl-acetamide;
(R)-2-[(4-Chloro-benzenesulfonyl)-(5-fluoro-2-trifluoromethyl-benzyl)-amino]-2-phenyl-acetamide;
(R)-2-[(4-Chloro-benzenesulfonyl)-(2-trifluoromethoxy-benzyl)-amino]-2-phenyl-acetamide;
(R)-4-{[(Carbamoyl-phenyl-methyl)-(4-chloro-benzenesulfonyl)-amino]-methyl}-3-methoxy-benzoic acid methyl ester;
(R)-2-[Biphenyl-2-ylmethyl-(4-chloro-benzenesulfonyl)-amino]-2-phenyl-acetamide;
(R)-2-[(2-Benzenesulfonylmethyl-benzyl)-(4-chloro-benzenesulfonyl)-amino]-2-phenyl-acetamide;
(R)-2-[(4-Chloro-benzenesulfonyl)-(2,3-difluoro-benzyl)-amino]-2-phenyl-acetamide;
(R)-2-[(4-Chloro-benzenesulfonyl)-(3,5-difluoro-benzyl)-amino]-2-phenyl-acetamide;
(R)-2-[(4-Chloro-benzenesulfonyl)-(2,3,6-trifluoro-benzyl)-amino]-2-phenyl-acetamide;
(R)-3-{[(Carbamoyl-phenyl-methyl)-(4-chloro-benzenesulfonyl)-amino]-methyl}-benzoic acid methyl ester;
(R)-2-[(4-Chloro-benzenesulfonyl)-(3,4-dichloro-benzyl)-amino]-2-phenyl-acetamide;
(R)-2-[(4-Chloro-benzenesulfonyl)-(2-fluoro-3-methyl-benzyl)-amino]-2-phenyl-acetamide;
(R)-2-[(4-Chloro-benzenesulfonyl)-(2,4,5-trifluoro-benzyl)-amino]-2-phenyl-acetamide;
(R)-2-[(4-Chloro-benzenesulfonyl)-(2,4,6-trifluoro-benzyl)-amino]-2-phenyl-acetamide;

(R)-2-[(4-Chloro-benzenesulfonyl)-(2-chloro-4-fluoro-benzyl)-amino]-2-phenyl-acetamide;
(R)-2-{(4-Chloro-benzenesulfonyl)-[3-(4-fluoro-phenoxy)-benzyl]-amino}-2-phenyl-acetamide;
(R)-2-[(4-Chloro-benzenesulfonyl)-(2'-cyano-biphenyl-4-ylmethyl)-amino]-2-phenyl-acetamide;
(R)-2-[(4-Chloro-benzenesulfonyl)-(4-methyl-benzyl)-amino]-2-phenyl-acetamide;
(R)-2-[(4-Chloro-benzenesulfonyl)-(3-nitro-benzyl)-amino]-2-phenyl-acetamide;
(R)-2-[(4-Chloro-benzenesulfonyl)-(2-methoxy-5-nitro-benzyl)-amino]-2-phenyl-acetamide;
(R)-2-[(4-Chloro-benzenesulfonyl)-(2-hydroxy-5-nitro-benzyl)-amino]-2-phenyl-acetamide;
(R)-2-[(4-Chloro-benzenesulfonyl)-(4-nitro-benzyl)-amino]-2-phenyl-acetamide;
(R)-2-[(4-Chloro-benzenesulfonyl)-(2,5-difluoro-benzyl)-amino]-2-phenyl-acetamide;
(R)-2-[(4-Bromo-2-fluoro-benzyl)-(4-chloro-benzenesulfonyl)-amino]-2-phenyl-acetamide;
(R)-2-[(4-Chloro-benzenesulfonyl)-(4-fluoro-2-trifluoromethyl-benzyl)-amino]-2-phenyl-acetamide;
(R)-2-[(4-Chloro-benzenesulfonyl)-(3-trifluoromethoxy-benzyl)-amino]-2-phenyl-acetamide;
(R)-2-[(4-Chloro-benzenesulfonyl)-(4,5-dimethoxy-2-nitro-benzyl)-amino]-2-phenyl-acetamide;
(R)-2-[(4-Chloro-benzenesulfonyl)-(3-methoxy-benzyl)-amino]-2-phenyl-acetamide;
(R)-2-[(4-Chloro-benzenesulfonyl)-(3,5-dimethoxy-benzyl)-amino]-2-phenyl-acetamide;
(R)-2-[(4-Chloro-benzenesulfonyl)-(4-trifluoromethylsulfanyl-benzyl)-amino]-2-phenyl-acetamide;
(R)-2-[(4-Chloro-benzenesulfonyl)-(4-pyrazol-1-yl-benzyl)-amino]-2-phenyl-acetamide;
(R)-2-[(4-Chloro-benzenesulfonyl)-(4-ethyl-benzyl)-amino]-2-phenyl-acetamide;
(R)-N-Butyl-4-{[(carbamoyl-phenyl-methyl)-(4-chloro-benzenesulfonyl)-amino]-methyl}-benzamide;
(R)-4-{[(Carbamoyl-phenyl-methyl)-(4-chloro-benzenesulfonyl)-amino]-methyl}-N-methyl-benzamide;
(R)-(4-{[(Carbamoyl-phenyl-methyl)-(4-chloro-benzenesulfonyl)-amino]-methyl}-phenyl)-acetic acid 2-oxo-2-phenyl-ethyl ester;
(R)-2-[(3,5-Bis-trifluoromethyl-benzyl)-(4-chloro-benzenesulfonyl)-amino]-2-phenyl-acetamide;
(R)-2-[(4-Benzoyl-benzyl)-(4-chloro-benzenesulfonyl)-amino]-2-phenyl-acetamide;
(R)-2-{(4-Chloro-benzenesulfonyl)-[3-(2-fluoro-phenoxy)-benzyl]-amino}-2-phenyl-acetamide;
(R)-2-[(4-Chloro-benzenesulfonyl)-(4-chloro-benzyl)-amino]-2-phenyl-acetamide;
(R)-2-[(4-Chloro-benzenesulfonyl)-(3,5-dimethyl-benzyl)-amino]-2-phenyl-acetamide;
(R)-2-[(4-Chloro-benzenesulfonyl)-(4-fluoro-3-trifluoromethyl-benzyl)-amino]-2-phenyl-acetamide;
(R)-4-{[(Carbamoyl-phenyl-methyl)-(4-trifluoromethoxy-benzenesulfonyl)-amino]-methyl}-benzoic acid methyl ester;
(R)-4-{[(Carbamoyl-phenyl-methyl)-(4-cyano-benzenesulfonyl)-amino]-methyl}-benzoic acid methyl ester;
(R)-4-{[(Carbamoyl-phenyl-methyl)-(3-chloro-4-methyl-benzenesulfonyl)-amino]-methyl}-benzoic acid methyl ester;
(R)-4-{[(Carbamoyl-phenyl-methyl)-(3-fluoro-benzenesulfonyl)-amino]-methyl}-benzoic acid methyl ester;
(R)-4-{[(Carbamoyl-phenyl-methyl)-(2,3,4-trifluoro-benzenesulfonyl)-amino]-methyl}-benzoic acid methyl ester;
(R)-4-{[(Carbamoyl-phenyl-methyl)-(3,4-difluoro-benzenesulfonyl)-amino]-methyl}-benzoic acid methyl ester;
(R)-4-{[(3-Bromo-benzenesulfonyl)-(carbamoyl-phenyl-methyl)-amino]-methyl}-benzoic acid methyl ester;
(R)-4-{[(Carbamoyl-phenyl-methyl)-(toluene-4-sulfonyl)-amino]-methyl}-benzoic acid methyl ester;
(R)-4-{[Benzenesulfonyl-(carbamoyl-phenyl-methyl)-amino]-methyl}-benzoic acid methyl ester;
(R)-4-{[(4-Bromo-benzenesulfonyl)-(carbamoyl-phenyl-methyl)-amino]-methyl}-benzoic acid methyl ester;
(R)-4-{[(Carbamoyl-phenyl-methyl)-(3-trifluoromethyl-benzenesulfonyl)-amino]-methyl}-benzoic acid methyl ester;
(R)-4-{[(Carbamoyl-phenyl-methyl)-(4-fluoro-benzenesulfonyl)-amino]-methyl}-benzoic acid methyl ester;
(R)-4-{[(Carbamoyl-phenyl-methyl)-(4-methoxy-benzenesulfonyl)-amino]-methyl}-benzoic acid methyl ester;
(R)-4-{[(Carbamoyl-phenyl-methyl)-(toluene-3-sulfonyl)-amino]-methyl}-benzoic acid methyl ester;
R)-4-{[(Carbamoyl-phenyl-methyl)-(2-chloro-benzenesulfonyl)-amino]-methyl}-benzoic acid methyl ester;
(R)-4-{[(Carbamoyl-phenyl-methyl)-(3-chloro-4-fluoro-benzenesulfonyl)-amino]-methyl}-benzoic acid methyl ester;
(R)-4-{[(Carbamoyl-phenyl-methyl)-(2,4-difluoro-benzenesulfonyl)-amino]-methyl}-benzoic acid methyl ester;
(R)-4-{[(Carbamoyl-phenyl-methyl)-(3,5-difluoro-benzenesulfonyl)-amino]-methyl}-benzoic acid methyl ester;
(R)-4-{[(Carbamoyl-phenyl-methyl)-(4-chloro-3-nitro-benzenesulfonyl)-amino]-methyl}-benzoic acid methyl ester;
(R)-4-{[(Carbamoyl-phenyl-methyl)-(5-fluoro-2-methyl-benzenesulfonyl)-amino]-methyl}-benzoic acid methyl ester;
(R)-4-{[(Carbamoyl-phenyl-methyl)-(2,3-dichloro-benzenesulfonyl)-amino]-methyl}-benzoic acid methyl ester;
(R)-4-{[(4-Bromo-2-methyl-benzenesulfonyl)-(carbamoyl-phenyl-methyl)-amino]-methyl}-benzoic acid methyl ester;
(R)-4-{[(Carbamoyl-phenyl-methyl)-(2-trifluoromethoxy-benzenesulfonyl)-amino]-methyl}-benzoic acid methyl ester;
(R)-4-{[(Carbamoyl-phenyl-methyl)-(3,4-dimethoxy-benzenesulfonyl)-amino]-methyl}-benzoic acid methyl ester;
(R)-4-{[(Carbamoyl-phenyl-methyl)-(4-chloro-2,5-dimethyl-benzenesulfonyl)-amino]-methyl}-benzoic acid methyl ester;
(R)-4-{[(Carbamoyl-phenyl-methyl)-(4-isopropyl-benzenesulfonyl)-amino]-methyl}-benzoic acid methyl ester;
(R)-4-{[(Carbamoyl-phenyl-methyl)-(4-propyl-benzenesulfonyl)-amino]-methyl}-benzoic acid methyl ester; and
(R)-4-{[(Carbamoyl-phenyl-methyl)-(3-nitro-benzenesulfonyl)-amino]-methyl}-benzoic acid methyl ester and pharmaceutically acceptable salts thereof.

15. A pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, comprising an amount of the compound according to claim 1 that is effective in inhibiting Aβ-peptide production or treating such disease and condition, and a pharmaceutically acceptable carrier.

16. A pharmaceutical composition for treating a disease or condition associated with the modulation of the Notch signaling pathway comprising the compound of Formula I according to claim 1, or their pharmaceutically acceptable salts.

17. The composition of claim 16, wherein the disease or condition is selected from the group consisting of cancer, arteriosclerosis, diabetic retinopathy, rheumatoid arthritis, psoriasis, inflammatory bowel disease, inflammation, asthma, graft rejection, graft versus host disease, autoimmune disease and transplant rejection.

18. The composition of claim 17, wherein the disease or condition is selected from the group consisting of cancer.

* * * * *